United States Patent
Yang et al.

(10) Patent No.: US 11,414,413 B2
(45) Date of Patent: Aug. 16, 2022

(54) HETEROCYCLIC COMPOUND AS JAK INHIBITOR, AND SALTS AND THERAPEUTIC USE THEREOF

(71) Applicant: Suzhou Longbiotech Pharmaceuticals Co., Ltd., Suzhou (CN)

(72) Inventors: Hengying Yang, Suzhou (CN); Sheng Kuang, Suzhou (CN); Shiwei Li, Suzhou (CN); Kuiwang Wu, Suzhou (CN); Shuxin Li, Suzhou (CN)

(73) Assignee: Suzhou Longbiotech Pharmaceuticals Co., Ltd., Suzhou (CN)

( * ) Notice: Subject to any disclaimer, the term of this patent is extended or adjusted under 35 U.S.C. 154(b) by 300 days.

(21) Appl. No.: 16/320,178

(22) PCT Filed: Jul. 25, 2017

(86) PCT No.: PCT/CN2017/094253
§ 371 (c)(1),
(2) Date: Jan. 24, 2019

(87) PCT Pub. No.: WO2018/019222
PCT Pub. Date: Feb. 1, 2018

(65) Prior Publication Data
US 2019/0270740 A1  Sep. 5, 2019

(30) Foreign Application Priority Data

Jul. 26, 2016 (CN) .......................... 201610590791.7
Jan. 19, 2017 (CN) .......................... 201710037675.7

(51) Int. Cl.
| | | |
|---|---|---|
| C07D 471/04 | (2006.01) | |
| A61P 37/02 | (2006.01) | |
| C07D 487/04 | (2006.01) | |
| A61P 35/00 | (2006.01) | |
| A61P 29/00 | (2006.01) | |
| C07D 401/04 | (2006.01) | |
| A61P 17/00 | (2006.01) | |
| A61P 19/02 | (2006.01) | |

(52) U.S. Cl.
CPC ............ *C07D 471/04* (2013.01); *A61P 17/00* (2018.01); *A61P 19/02* (2018.01); *A61P 29/00* (2018.01); *A61P 35/00* (2018.01); *A61P 37/02* (2018.01); *C07D 401/04* (2013.01); *C07D 487/04* (2013.01)

(58) Field of Classification Search
CPC .................................................. C07D 471/04
See application file for complete search history.

(56) References Cited

U.S. PATENT DOCUMENTS

| | | |
|---|---|---|
| 7,598,257 B2 | 10/2009 | Rodgers et al. |
| 2007/0208053 A1 | 9/2007 | Arnold et al. |
| 2009/0088445 A1 | 4/2009 | Ledeboer et al. |
| 2010/0311693 A1 | 12/2010 | Curry et al. |
| 2010/0331319 A1 | 12/2010 | Menet |
| 2011/0190260 A1 | 8/2011 | Menet et al. |
| 2012/0277247 A1 | 11/2012 | Menet et al. |

FOREIGN PATENT DOCUMENTS

| | | |
|---|---|---|
| CN | 101228161 A | 7/2008 |
| CN | 101374839 A | 2/2009 |
| CN | 101448826 A | 6/2009 |
| CN | 101801971 A | 8/2010 |
| CN | 102026999 A | 4/2011 |
| CN | 102105471 A | 6/2011 |
| CN | 102459258 A | 5/2012 |
| CN | 102482273 A | 5/2012 |
| CN | 103254190 A | 8/2013 |
| CN | 103764654 A | 4/2014 |
| CN | 106905322 A | 6/2017 |
| CN | 107531695 A | 1/2018 |
| EP | 2445912 B1 | 8/2014 |
| EP | 2445911 B1 | 3/2017 |
| EP | 3290418 A1 | 3/2018 |

(Continued)

OTHER PUBLICATIONS

NPL1-Database Registry [Online] Chemical Abstracts Service, Columbus, Ohio, US; Jun. 6, 2014 (Jun. 6, 2014), "7H-Pyrrolo [2,3-d]pyrimidine, 4-[4-[1-(1-piperidinyl)ethyl]phenyl]-", XP002793677, Database accession No. 1609835-65-5; 1 pg.

(Continued)

*Primary Examiner* — Paul V Ward
(74) *Attorney, Agent, or Firm* — Fox Rothschild LLP

(57) ABSTRACT

Disclosed are a heterocyclic derivative as a JAK inhibitor, and salts thereof, wherein the definitions of (II), (III) and R are described in detail in the specification. In addition, also disclosed are a medicine including the compound and salts thereof as an active ingredient, and the use thereof in the preparation of a medicine for treating JAK-related target diseases, such as immune system diseases, rheumatoid arthritis and tumors.

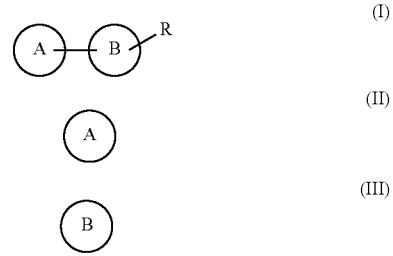

6 Claims, No Drawings

(56) References Cited

FOREIGN PATENT DOCUMENTS

| | | | |
|---|---|---|---|
| EP | 3409673 | A1 | 12/2018 |
| EP | 3492469 | A1 | 6/2019 |
| JP | 2009519340 | A | 5/2009 |
| JP | 2009523812 | A | 6/2009 |
| JP | 2009532475 | A | 9/2009 |
| JP | 2011529032 | A | 12/2011 |
| JP | 2012528886 | A | 11/2012 |
| JP | 2012530766 | A | 12/2012 |
| JP | 2014512405 | A | 5/2014 |
| JP | 2019503395 | A | 2/2019 |
| WO | 2007041130 | A2 | 4/2007 |
| WO | 2007070514 | A1 | 6/2007 |
| WO | 2007084557 | A2 | 7/2007 |
| WO | 2007084667 | A2 | 7/2007 |
| WO | 2007117494 | A1 | 10/2007 |
| WO | 2009114512 | A1 | 9/2009 |
| WO | 2010010184 | A1 | 1/2010 |
| WO | 2010010186 | A1 | 1/2010 |
| WO | 2010010190 | A1 | 1/2010 |
| WO | 2010141796 | A2 | 12/2010 |
| WO | 2012146659 | A1 | 11/2012 |
| WO | 2013019828 | A1 | 2/2013 |
| WO | 2013173506 | A2 | 11/2013 |
| WO | 2016173484 | A1 | 11/2016 |
| WO | 2017129116 | A1 | 8/2017 |

OTHER PUBLICATIONS

MPL2-Database Registry [Online] Chemical Abstracts Service, Columbus, Ohio, US; Mar. 21, 2011 (Mar. 21, 2011), "7H-Pyrrolo[2,3-d]pyrimidine, 4-[4-[1-(4-morpholinyl)ethyl]phenyl]-",XP002793678, Database accession No. 1269210-01-6.

Office Action issue in related European Application No. 17 833 526.1 dated Jul. 23, 2020; 7 pgs.

Database Registry [Online], Chemical Abstracts Service, (2012); Database accession No. 1360287-34-8, Abstract, 1 pg.

Supplementary European Search Report from related European Application No. 17 83 3525, dated Mar. 2, 2020; 27 pgs.

Office Action issued by the Chinese Patent Office in the Chinese application No. 201780044487.5 and its English translation; dated Dec. 29, 2020.

Office Action issued by the Chinese Patent Office in the Chinese application No. 201780044794.3 and its English translation; dated Jan. 7, 2021.

Christel J. Menet et al. "Triazolopyridines Selective JAK1 Inhibitors: From Hit Identification to GLPG0634" J. Med. Chem. vol. 57, Nov. 4, 2014 pp. 9323-9342.

Office Action dated May 25, 2021 in related JP Apln No. 2019-504824; 11 pgs.

Office Action dated Jun. 22, 2021 in related JP Apln No. 2019-504825; 16 pgs.

HETEROCYCLIC COMPOUND AS JAK INHIBITOR, AND SALTS AND THERAPEUTIC USE THEREOF

CROSS REFERENCE TO RELATED APPLICATIONS

The present application is a national application of PCT/CN2017/094253 filed on Jul. 25, 2017, which claims the priorities of the Chinese Patent Application No. 201610590791.7 filed on Jul. 26, 2016 and the Chinese Patent Application No. 201710037675.7 filed on Jan. 19, 2017. The Chinese Patent Applications No. 201610590791.7 and No. 201710037675.7 are incorporated herein by reference as part of the disclosure of the present application.

FIELD OF THE INVENTION

The present disclosure relates to a class of heterocyclic compounds as JAK inhibitors, salts thereof and medicaments containing the said compounds or salts thereof as active ingredients, and relates to use of the same in the preparation of medicaments for treating JAK-related target diseases such as immune system diseases, rheumatoid arthritis and tumors.

BACKGROUND OF THE INVENTION

The JAK-STAT signaling pathway is a cytokine-stimulated signal transduction pathway discovered in recent years, wherein JAK plays an important role in cytokine signaling. The downstream substrates of the kinase JAK family include signal transducers and activators of transcription (STAT). JAK protein is an important member in this pathway, and the abnormal increase in its activity often leads to onset of diseases. Many diseases are related to abnormal cellular responses of JAK-STAT signaling pathway, including autoimmune diseases, inflammatory diseases, bone diseases, metabolic diseases, neurological and neurodegenerative diseases, cancers, cardiovascular diseases, allergy and asthma, and Alzheimer's disease.

Rheumatoid arthritis (RA) is a chronic autoimmune disease commonly observed in clinic, which is mainly characterized by joint swelling, pain, stiffness, deformity and severe functional impairment. The population incidence rate of RA is 0.5%-1.0%. Because the pathogenesis of RA is not clear, its pathological process is difficult to control, and the disability rate is high, which seriously impairs the physical and mental health of patients and reduces the quality of life of patients. The drugs currently used to treat RA are mainly non-steroidal anti-inflammatory drugs (NSAIDs), disease-modifying antirheumatic drugs (DMARDs), and antibody drugs. For a long time, the first-line drugs for the treatment of RA were DMARDs. In 1988, the first DMARD drug methotrexate (MTX) was approved by the FDA for the treatment of RA, rendering MTX an important milestone in the history of RA treatment. The drug is widely used due to its advantages such as effectiveness, tolerability, safety, etc., but it has adverse effects including nausea, vomiting, stomach discomfort, and hepatotoxicity. In contrast, newly developed antibody drugs have good efficacy and safety indicators for moderate to severe RA. However, because it targets specific cytokines, the population benefit from it is significantly limited, and meanwhile the cost of treatment and administration of injection also limit the promotion of such drugs.

In the past 20 years, the treatment of RA has achieved great improvement, and the patient's condition can be effectively controlled by the existing treatment regimen. However, RA patients are yet experiencing problems such as recurrence of the disease, unsatisfactory treatment effect, poor long-term tolerance, and some adverse effects. More importantly, the quality of life of RA patients, including function of organs such as joints, has not been really improved by existing treatments. Therefore, there is still huge unmet clinical needs in this field regarding restoring the normal function of patients.

Studies have shown that the core treatment of RA is the production of a large number of cytokines by autocrine of mononuclear/macrophages, lymphocytes, etc. infiltrated in RA synovial tissue and cells. These cytokines interact and activate JAK/STAT signaling pathway (Januskinase/Signal transducer and activators of transcription signaling pathway) through different ways. By specifically inhibiting the JAK/STAT signaling pathway, the cascade amplification of these cytokines can be blocked, thereby improving the symptoms of damaged joints in RA patients. Therefore, the JAK/STAT signaling pathway is a potential target for the treatment of RA. In November 2012, the oral JAK inhibitor Tofacitinib was first approved by the FDA for the treatment of rheumatoid arthritis (RA), becoming the first successful kinase inhibitor drug in the field.

The JAK-STAT signaling pathway is a cytokine-stimulated signal transduction pathway discovered in recent years, wherein JAK plays an important role in cytokine signaling. JAK kinase (abbreviated as JAKs, including four known members JAK1, JAK2, JAK3, TYK2) is a small family of cytoplasmic non-receptor tyrosine protein kinase superfamilies JAK3 is distributed in the bone marrow and lymphatic system, and JAK1, TYK2, and JAK2 are widely distributed in various tissue cells. When JAKs bind to cytokine receptors on the cell surface, the receptor-coupled JAKs are activated, and in turn the receptors are phosphorylated. This provides a recruitment site for cytoplasmic signal transducers and activators of transcription STAT protein (abbreviated as STAT, including STAT1-4, STAT5a, STAT5b, STAT6). JAKs phosphorylate the STAT protein, and the latter is transferred into the nucleus to regulate gene expression after dimerization. This pathway is JAK/STAT signaling pathway (O'Shea J. J., et al., N. Engl. J. Med., 2013, 368:161-170).

The JAK/STAT signaling pathway is a signaling pathway stimulated by a variety of cytokines and growth factor receptors, including interleukins, interferons (IFN-α, IFN-β, IFN-γ), erythropoietin (EPO), granulocyte-macrophage colony stimulating factor (GM-CSF), somatotropin (GH), prolactin (PRL), thrombopoietin (TPO), etc., which plays a key role in the proliferation of immune cells and hematopoietic stem cells, and the biological process of immune regulation (Ghoreschi K., et al., Immunol. Rev., 2009, 228:273-287).

JAK1 can bind to IL-10, IL-19, IL-20, IL-22, IL-26, IL-28, IFN-a, IFN-γ, IL-6 in the gp130 family, and other receptors containing γc, etc. (Rodig S. J., et al., Cell, 1998, 93:373-383). JAK1 knockout experiments on mouse models indicate that this enzyme plays a key role in regulating the biological effects of the various cytokine receptors described above (Kisseleva T., et al., Gene, 2002, 285:1-24). JAK1 is a novel target in the field of diseases such as immune-related diseases, inflammation and cancer. JAK1 inhibitors can be used to treat/prevent autoimmune diseases and inflammation (Hornakova T., et al., Blood, 2010, 115:3287-3295), such as leukemia, lymphoma, melanoma, arthritis, psoriasis, Crohn's disease, lupus erythematosus, acquired immunodeficiency syndrome (Hou S., et al., Hum. Genet., 2013, 132:1049-1058) and the like.

JAK2 plays an important role in the regulation of various receptor signals including IL-3, IFN-γ, EPO, GH and the like (Levy D. E., et al., Nat. Rev. Mol. Cell Biol., 2002, 3:651-662). Knocking out JAK2 in a mouse model can lead to the death of anemia animals (Schindler C., et al., J. Biol. Chem., 2007, 282:20059-20063); a base mutation JAK2V617F on the JAK2 gene in humans is closely related to the occurrence of polycythemia vera (PV) and essential thrombocythemia (ET) in myeloproliferative diseases, etc. (Ghoreschi K., et al., Immunol. Rev., 2009, 228:273-287).

JAK3 regulates cell signaling by binding to the gamma co-chain (γc) in cytokine receptor complexes such as IL-2, IL-4, IL-7, IL-9, IL-15, IL-21. Both JAK3 and γc mutations can lead to severe combined immunodeficiency (SCID) (Villa A., et al., Blood, 1996, 88:817-823). Abnormal JAK3 activity is characterized by a large decrease in T cells and NK cells, and loss of B cell function, which severely affects the normal biological functions of the immune system. Based on its functional characteristics and special tissue distribution, JAK3 has become an attractive drug target for immune system-related diseases. Its inhibitors have great value of clinical application in the treatment/prevention of rheumatoid arthritis (RA), Crohn's disease, systemic lupus erythematosus, multiple sclerosis, type I diabetes, psoriasis, allergic diseases, asthma, chronic obstructive pulmonary disease, leukemia, lymphoma, organ transplantation and other diseases (Papageorgiou A. C., et al., 2004, Trends Pharm. Sci., 2004, 25:558-562).

TYK2 is the first member of the JAK family and can be activated by a variety of receptors such as interferons (IFNs), IL-10, IL-12, IL-23, IL-27, and the like. In mice, loss of TYK2 function can cause defects in the signaling pathways of various cytokine receptors, leading to viral infection, decreased antibacterial and immune function, and increased likelihood of pulmonary infection (Kisseleva T., et al., 2002, Gene, 285:1-24). In addition, studies from the Lamer A.C group have shown that TYK2 can help inhibit the growth and metastasis of breast cancer (Zhang Q., et al., 2011, J. Interferon Cytokine Res., 31:671-677).

Because JAK kinase is involved in various important physiological processes in the body, extensive inhibition of different subtypes may have adverse effects. Tofacitinib is used in patients with moderate to severe RA with insufficient MTX response or intolerance. It was observed that it has certain adverse effects in clinical trials, including infection, tuberculosis, tumor, anemia, liver damage, increased cholesterol and the like. Tofacitinib has significant inhibitory activity on JAK1, JAK2, and JAK3 subtypes. Because JAK2 activity is associated with red blood cell differentiation and lipid metabolism, some of the above adverse effects are thought to be related to the non-selective inhibition profile of the drug. Therefore, the search for selective JAK1 and/or JAK3 inhibitors will become a new direction of RA drug research.

Currently, JAK inhibitors have been proven to be useful in medicaments for the treatment of blood system diseases, tumors, rheumatoid arthritis, psoriasis and the like. Because of the significant medical use of JAK inhibitors in medicaments for a variety of related diseases, research and discovery of such compounds are extremely beneficial.

SUMMARY OF THE INVENTION

The first object of the present disclosure is to provide a class of heterocyclic derivatives as JAK inhibitors.

In particular, provided herein are a class of heterocyclic derivatives having the structure of formula (I) as a JAK inhibitor:

Formula (I)

and isomers, solvates, or pharmaceutically acceptable salts thereof.

When $\hat{B}$ is selected from:

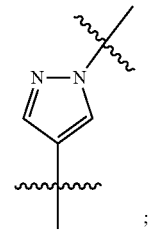 [SMILES: *c1cnn(*)c1]

R is selected from:

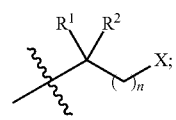

when X is —CONH—$R^4$, $R^4$ is hydrogen, $C_1$-$C_6$ alkyl, or $C_3$-$C_6$ cycloalkyl, and may be optionally substituted by halogen;

$\hat{A}$ is selected from:

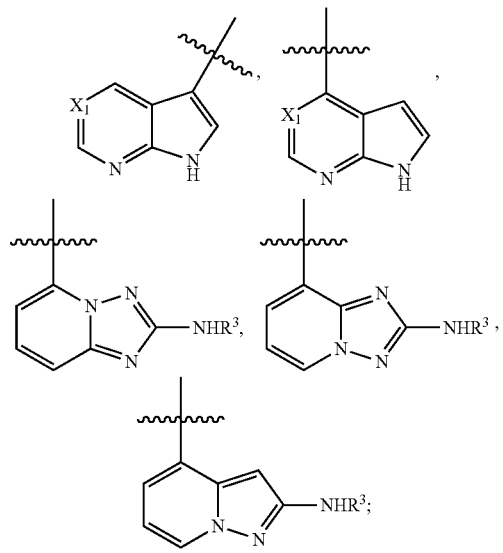

$R^1$, $R^2$ are independently selected from hydrogen, $C_1$-$C_6$ alkyl, and may be substituted by $C_1$-$C_6$ alkoxy, $C_1$-$C_6$ alkylsulfonyl; $R^1$, $R^2$ may also form a 4-10 membered heterocyclic ring with the carbon atom to which they are attached, and the ring carbon atom may be replaced by N, O, S, —SO$_2$—; wherein the ring may be substituted by C$_1$-C$_6$ alkylsulfonyl, C$_1$-C$_6$ alkyl, C$_1$-C$_6$ alkylacyl;

R$^3$ is hydrogen, C$_1$-C$_7$ alkylacyl, or C$_3$-C$_7$ cycloalkylacyl;

n is selected from 0, 1, 2, 3, 4, 5;

X$_1$ is N, —CR$^5$;

R$^5$ is H, —CN, or halogen;

When X is —CN, is selected from:

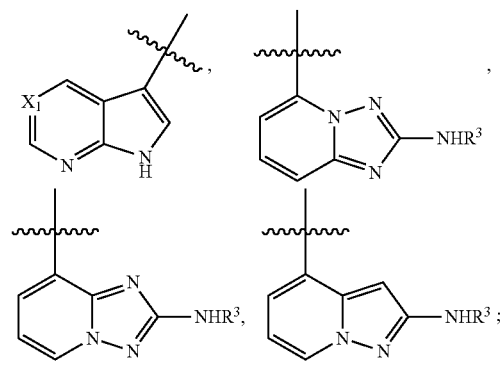

wherein:

R$^1$, R$^2$ are hydrogen, C$_1$-C$_6$ alkyl, and may be substituted by C$_1$-C$_6$ alkoxy, C$_1$-C$_6$ alkylsulfonyl, when R$^1$, R$^2$ form a 4-10 membered ring with the carbon atom to which they are attached, the ring may be substituted by C$_1$-C$_6$ alkyl, C$_1$-C$_6$ alkylsulfonyl, C$_1$-C$_6$ alkylacyl; wherein the C$_1$-C$_6$ alkyl, C$_1$-C$_6$ alkylsulfonyl, or C$_1$-C$_6$ alkylacyl may be optionally substituted by halogen;

is selected from:

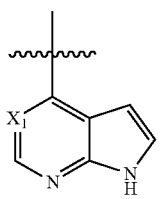

At this time, R$^1$ and R$^2$ form a 5-8 membered ring with the carbon atom to which they are attached, and the ring carbon atom may be replaced by N, O, S, or —SO$_2$—; and the ring may be substituted by C$_1$-C$_6$ alkyl, C$_1$-C$_6$ alkylsulfonyl;

When B̂ is selected from:

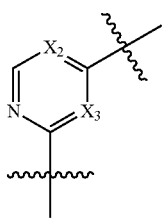

X$_2$ is N, CR$^6$;

X$_3$ is N, CR$^7$;

R$^6$, R$^7$ are independently selected from hydrogen, —CN, halogen;

is selected from:

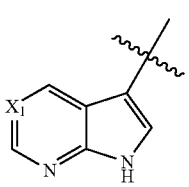 , 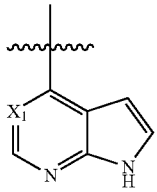

X$_1$ is N, or —CR$^5$;

R$^5$ is H, —CN, or halogen;

R is selected from:

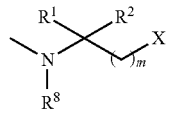

When X is selected from —CONH—R$^4$; R$^4$ is hydrogen, C$_1$-C$_6$ alkyl, C$_3$-C$_6$ cycloalkyl, and may be optionally substituted by halogen;

R$^1$, R$^2$ form a 4-10 membered ring with the carbon atom to which they are attached, and the ring carbon atom may be replaced by N, O, S, or —SO$_2$—, and the ring may be substituted by C$_1$-C$_6$ alkyl, C$_1$-C$_6$ alkylsulfonyl, or C$_1$-C$_6$ alkylacyl;

When X is —CN,

R$^1$, R$^2$ are independently selected from hydrogen, C$_1$-C$_6$ alkyl, and may be substituted by C$_1$-C$_6$ alkoxy, C$_1$-C$_6$ alkylsulfonyl, aryl, heteroaryl, R$^1$, R$^2$ may also form a 4-10 membered ring with the carbon atom to which they are attached; the ring carbon atom may be replaced by N, O, S, or —SO$_2$—, and the ring may be substituted by alkylsulfonyl, C$_1$-C$_6$ alkyl, C$_1$-C$_6$ alkylacyl; one of R$^1$ and R$^2$ may also be bonded to R$^8$ to form a 4-6 membered ring;

R$^8$ is hydrogen or C$_1$-C$_6$ alkyl group;

m is selected from 0, 1, 2, 3, 4, 5.

Specifically, the compound disclosed herein has the structure of formula (II):

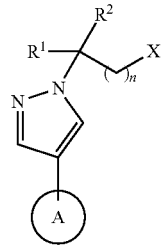

Formula (II)

and isomers, solvates, or pharmaceutically acceptable salts thereof;

wherein:

When X is —CONH—R$^4$; R$^4$ is hydrogen, C$_1$-C$_6$ alkyl, or C$_3$-C$_6$ cycloalkyl, and may be optionally substituted by halogen;

Â is selected from:

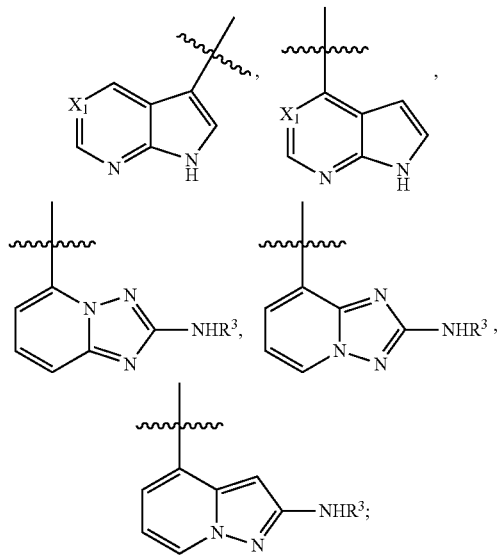

$R^1$, $R^2$ are independently selected from hydrogen, $C_1$-$C_6$ alkyl, and may be substituted by $C_1$-$C_6$ alkoxy, $C_1$-$C_6$ alkylsulfonyl; $R^1$, $R^2$ may also form a 4-10 membered heterocyclic ring with the carbon atom to which they are attached, wherein the ring carbon atom may be replaced by N, O, S, or —$SO_2$—, and the ring may be substituted by C—$C_6$ alkylsulfonyl, $C_1$-$C_6$ alkyl, or $C_1$-$C_6$ alkylacyl;

$R^3$ is hydrogen, $C_1$-$C_7$ alkylacyl, or $C_3$-$C_7$ cycloalkylacyl;

n is selected from 0, 1, 2, 3, 4, 5;

$X_1$ is N, or —$CR^5$;

$R^5$ is H, —CN, or halogen;

When X is —CN,

Â is selected from:

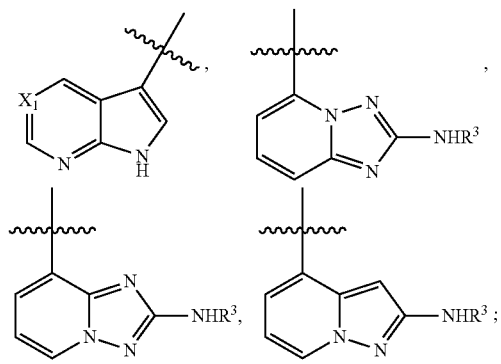

wherein:

$R^1$, $R^2$ are hydrogen, $C_1$-$C_6$ alkyl, and may be substituted by $C_1$-$C_6$ alkoxy or $C_1$-$C_6$ alkylsulfonyl, when $R^1$, $R^2$ form a 4-10 membered ring with the carbon atom to which they are attached, the ring may be substituted by $C_1$-$C_6$ alkyl, $C_1$-$C_6$ alkylsulfonyl, $C_1$-$C_6$ alkylacyl, wherein the $C_1$-$C_6$ alkyl, $C_1$-$C_6$ alkylsulfonyl, $C_1$-$C_6$ alkylacyl may be optionally substituted by halogen;

When Â is selected from:

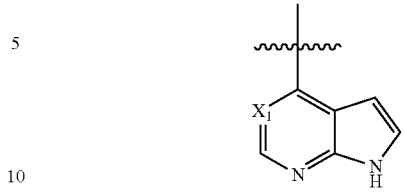

$R^1$ and $R^2$ form a 5-8 membered ring with the carbon atom to which they are attached, wherein the ring carbon atom may be replaced by N, O, S, or —$SO_2$—, and the ring may be substituted by $C_1$-$C_6$ alkyl, or $C_1$-$C_6$ alkylsulfonyl;

Preferably, the compound of formula (II) disclosed herein is selected from, but not limited to, the following structure:

2-(3-(4-(1H-pyrrolo[2,3-b]pyridin-3-yl)-1H-pyrazol-1-yl)-1-(ethylsulfonyl)azetidin-3-yl)acetonitrile;

2-(4-(4-(7H-pyrrolo[2,3-d]pyrimidin-4-yl)-1H-pyrazol-1-yl)-1,1-dioxotetrahydro-2H-thiopyran-4-yl)acetonitrile 2-(4-(4-(1H-pyrrolo[2,3-b]pyridin-4-yl)-1H-pyrazol-1-yl)-1,1-dioxotetrahydro-2H-thiopyran-4-yl)acetonitrile 2-(4-(4-(1H-pyrrolo[2,3-b]pyridin-3-yl)-1H-pyrazol-1-yl)-1,1-dioxotetrahydro-2H-thiopyran-4-yl)acetonitrile;

2-(4-(4-(1H-pyrrolo[2,3-b]pyridin-3-yl)-1H-pyrazol-1-yl)-1-(methylsulfonyl)piperidin-4-yl)-N-(2,2,2-trifluoroethyl)acetonitrile;

2-(3-(4-(1H-pyrrolo[2,3-b]pyridin-3-yl)-1H-pyrazol-1-yl)-1-(ethylsulfonyl)azetidin-3-yl)acetamide;

2-(3-(4-(1H-pyrrolo[2,3-b]pyridin-3-yl)-1H-pyrazol-1-yl)-1-(ethylsulfonyl)azetidin-3-yl)-N-(2,2,2-trifluoroethyl)acetamide;

2-(3-(4-(1H-pyrrolo[2,3-d]pyrimidin-4-yl)-1H-pyrazol-1-yl)-1-(ethylsulfonyl) azetidin-3-yl)-N-(2,2,2-trifluoroethyl)acetamide;

2-(3-(4-(1H-pyrrolo[2,3-b]pyridin-4-yl)-1H-pyrazol-1-yl)-1-(ethylsulfonyl)azetidin-3-yl)-N-(2,2,2-trifluoroethyl)acetamide;

2-(3-(4-(1H-pyrrolo[2,3-b]pyridin-4-yl)-1H-pyrazol-1-yl)-1-(ethylsulfonyl)azetidin-3-yl)-N-methylacetamide;

2-(3-(4-(1H-pyrrolo[2,3-b]pyridin-4-yl)-1H-pyrazol-1-yl)-1-(ethylsulfonyl)azetidin-3-yl)acetamide;

2-(3-(4-(7H-pyrrolo[2,3-d]pyrimidin-4-yl)-1H-pyrazol-1-yl)-1-(methylsulfonyl)azetidin-3-yl)-N-(2,2,2-trifluoroethyl)acetamide;

2-(3-(4-(7H-pyrrolo[2,3-d]pyrimidin-4-yl)-1H-pyrazol-1-yl)-1-(methylsulfonyl)azetidin-3-yl)-N-methylacetamide;

2-(3-(4-(7H-pyrrolo[2,3-d]pyrimidin-4-yl)-1H-pyrazol-1-yl)-1-(methylsulfonyl)azetidin-3-yl)acetamide;

2-(3-(4-(1H-pyrrolo[2,3-b]pyridin-4-yl)-1H-pyrazol-1-yl)-1-(methylsulfonyl)azetidin-3-yl)-N-(2,2,2-trifluoroethyl)acetamide;

2-(3-(4-(1H-pyrrolo[2,3-b]pyridin-4-yl)-1H-pyrazol-1-yl)-1-(methylsulfonyl)azetidin-3-yl)-N-methylacetamide;

2-(3-(4-(1H-pyrrolo[2,3-b]pyridin-4-yl)-1H-pyrazol-1-yl)-1-(methylsulfonyl)azetidin-3-yl)acetamide;

2-(4-(4-(1H-pyrrolo[2,3-b]pyridin-3-yl)-1H-pyrazol-1-yl)-1,1-dioxotetrahydro-2H-thiopyran-4-yl)acetamide 2-(4-(4-(1H-pyrrolo[2,3-b]pyridin-3-yl)-1H-pyrazol-1-yl)-1,1-dioxotetrahydro-2H-thiopyran-4-yl)-N-(2,2,2-trifluoroethyl)acetamide;

2-(4-(4-(7H-pyrrolo[2,3-d]pyrimidin-4-yl)-1H-pyrazol-1-yl)-1,1-dioxotetrahydro-2H-thiopyran-4-yl)-N-(2,2,2-trifluoroethyl)acetamide;

2-(4-(4-(7H-pyrrolo[2,3-b]pyridin-4-yl)-1H-pyrazol-1-yl)-1,1-dioxotetrahydro-2H-thiopyran-4-yl)-N-(2,2,2-trifluoroethyl)acetamide;

2-(4-(4-(7H-pyrrolo[2,3-b]pyridin-3-yl)-1H-pyrazol-1-yl)-1-(methylsulfonyl)piperidin-4-yl)-N-(2,2,2-trifluoroethyl)acetamide;

2-(4-(4-(7H-pyrrolo[2,3-b]pyrimidin-4-yl)-1H-pyrazol-1-yl)-1-(methylsulfonyl)piperidin-4-yl)-N-(2,2,2-trifluoroethyl)acetamide;

2-(4-(4-(7H-pyrrolo[2,3-b]pyridin-4-yl)-1H-pyrazol-1-yl)-1-(methylsulfonyl)piperidin-4-yl)-N-(2,2,2-trifluoroethyl)acetamide;

2-(1-(4-(1H-pyrrolo[2,3-b]pyridin-3-yl)-1H-pyrazol-1-yl)cyclopentyl)-N-(2,2,2-trifluoroethyl)acetamide;

2-(1-(4-(1H-pyrrolo[2,3-b]pyrimidin-4-yl)-1H-pyrazol-1-yl)cyclopentyl)-N-(2,2,2-trifluoroethyl)acetamide;

2-(1-(4-(1H-pyrrolo[2,3-b]pyrimidin-4-yl)-1H-pyrazol-1-yl)cyclopentyl)-N-(2,2,2-trifluoroethyl)acetamide;

3-(4-(1H-pyrrolo[2,3-b]pyridin-3-yl)-1H-pyrazol-1-yl)-3-methyl-N-(2,2,2-trifluoroethyl)butanamide;

3-(4-(7H-pyrrolo[2,3-b]pyrimidin-4-yl)-1H-pyrazol-1-yl)-3-methyl-N-(2,2,2-trifluoroethyl)butanamide;

3-(4-(7H-pyrrolo[2,3-b]pyridin-4-yl)-1H-pyrazol-1-yl)-3-methyl-N-(2,2,2-trifluoroethyl)butanamide;

and isomers, solvates, or pharmaceutically acceptable salts thereof.

Specifically, the compound disclosed herein has the structure of formula (III):

Formula (III)

wherein:

$X_2$ is N, or $CR^6$;

$X_3$ is N, or $CR^7$;

$R^6$, $R^7$ are independently selected from H, —CN, or halogen;

Â is selected from:

$X_1$ is N, or —$CR^5$;

$R^5$ is H, —CN, or halogen;

When X is selected from —CONH—$R^4$;

$R^1$, $R^2$ form a 4-10 membered ring with the co-linked carbon atom, wherein the ring carbon atom may be replaced by N, O, S, —$SO_2$—, and the ring may be substituted by $C_1$-$C_6$ alkyl, $C_1$-$C_6$ alkylsulfonyl, $C_1$-$C_6$ alkylacyl;

$R^4$ is hydrogen, $C_1$-$C_6$ alkyl, $C_3$-$C_6$ cycloalkyl, and may be optionally substituted by halogen;

When X is —CN, $R^1$, $R^2$ are independently selected from hydrogen, $C_1$-$C_6$ alkyl, and may be substituted by $C_1$-$C_6$ alkoxy, $C_1$-$C_6$ alkylsulfonyl, aryl, or heteroaryl, $R^1$, $R^2$ may also form a 4-10 membered ring with the carbon atom to which they are attached, wherein the ring carbon atom may be replaced by N, O, S, or —$SO_2$—, and the ring may be substituted by an alkylsulfonyl, $C_1$-$C_6$ alkyl, $C_1$-$C_6$ alkylacyl; one of $R^1$ and $R^2$ may also be bonded to $R^8$ to form a 4-6 membered ring;

$R^8$ is hydrogen or $C_1$-$C_6$ alkyl;

m is selected from 0, 1, 2, 3, 4, 5;

Preferably, the compound of formula (III) disclosed herein is selected from, but not limited to, the following structure:

3-((2-(1H-pyrrolo[2,3-b]pyridin-3-yl)pyrimidin-4-yl)amino)-1-(methylsulfonyl-N-(2,2,2-trifluoroethyl)azetidin-3-carboxamide;

3-((2-(1H-pyrrolo[2,3-b]pyridin-3-yl)pyrimidin-4-yl)amino)-1-(ethylsulfonyl)-N-(2,2,2-trifluoroethyl)azetidin-3-carboxamide;

3-((2-(1H-pyrrolo[2,3-b]pyridin-3-yl)pyrimidin-4-yl)amino)-1-(cyclopropylsulfonyl)-N-(2,2,2-trifluoroethyl)azetidin-3-carboxamide;

3-(5-fluoro-2-(1H-pyrrolo[2,3-b]pyridin-3-yl)pyrimidin-4-yl)amino)-1-(methylsulfonyl)-N-(2,2,2-trifluoroethyl)azetidin-3-carboxamide;

3-(5-fluoro-2-(1H-pyrrolo[2,3-b]pyridin-3-yl)pyrimidin-4-yl)amino)-1-(ethylsulfonyl)-N-(2,2,2-trifluoroethyl)azetidin-3-carboxamide;

3-(5-fluoro-2-(1H-pyrrolo[2,3-b]pyridin-3-yl)pyrimidin-4-yl)amino)-1-(cyclopropylsulfonyl)-N-(2,2,2-trifluoroethyl)azetidin-3-carboxamide;

4-((2-(1H-pyrrolo[2,3-b]pyridin-3-yl)pyrimidin-4-yl)amino)-1-(methylsulfonyl)-N-(2,2,2-trifluoroethyl)piperidin-4-carboxamide;

4-((2-(1H-pyrrolo[2,3-b]pyridin-3-yl)pyrimidin-4-yl)amino)-1-(ethylsulfonyl)-N-(2,2,2-trifluoroethyl)piperidin-4-carboxamide;

4-((2-(1H-pyrrolo[2,3-b]pyridin-3-yl)pyrimidin-4-yl)amino)-1-(cyclopropylsulfonyl)-N-(2,2,2-trifluoroethyl)piperidin-4-carboxamide;

4-((5-fluoro-2-(1H-pyrrolo[2,3-b]pyridin-3-yl)pyrimidin-4-yl)amino)-1-(methylsulfonyl)-N-(2,2,2-trifluoroethyl)piperidin-4-carboxamide;

4-((5-fluoro-2-(1H-pyrrolo[2,3-b]pyridin-3-yl)pyrimidin-4-yl)amino)-1-(ethyl sulfonyl)-N-(2,2,2-trifluoroethyl)piperidin-4-carboxamide;

4-((5-fluoro-2-(1H-pyrrolo[2,3-b]pyridin-3-yl)pyrimidin-4-yl)amino)-1-(cyclo propylsulfonyl)-N-(2,2,2-trifluoroethyl)piperidin-4-carboxamide;

4-((2-(1H-pyrrolo[2,3-b]pyridin-3-yl)pyrimidin-4-yl)amino)-N-(2,2,2-trifluoroethyl)tetrahydro-2H-thiopyran-4-carboxamide 1,1-dioxide;

4-((5-fluoro-2-(1H-pyrrolo[2,3-b]pyridin-3-yl)pyrimidin-4-yl)amino)-N-(2,2,2-trifluoroethyl)tetrahydro-2H-thiopyran-4-carboxamide 1,1-dioxide;

3-((2-(1H-pyrrolo[2,3-b]pyridin-3-yl)pyrimidin-4-yl)amino)-1-(ethylsulfonyl) azetidine-3-carbonitrile;

3-((2-(7H-pyrrolo[2,3-d]pyrimidin-4-yl)pyrimidin-4-yl)amino)-1-(ethylsulfonyl)azetidine-3-carbonitrile;

3-((2-(1H-pyrrolo[2,3-b]pyridin-4-yl)pyrimidin-4-yl)amino)-1-(ethylsulfonyl) azetidine-3-carbonitrile;

3-((2-(1H-pyrrolo[2,3-b]pyridin-3-yl)pyrimidin-4-yl)amino)-1-(methylsulfonyl)azetidine-3-carbonitrile;

3-((2-(7H-pyrrolo[2,3-d]pyrimidin-4-yl)pyrimidin-4-yl)amino)-1-(methylsulfonyl)azetidine-3-carbonitrile;

3-((2-(1H-pyrrolo[2,3-b]pyridin-4-yl)pyrimidin-4-yl)amino)-1-(methylsulfonyl)azetidine-3-carbonitrile;

4-((2-(1H-pyrrolo[2,3-b]pyridin-3-yl)pyrimidin-4-yl) amino)tetrahydro-2H-thiopyran-4-carbonitrile 1,1-dioxide;

4-((2-(7H-pyrrolo[2,3-d]pyrimidin-4-yl)pyrimidin-4-yl) amino)tetrahydro-2H-thiopyran-4-carbonitrile 1,1-dioxide;

4-((2-(1H-pyrrolo[2,3-b]pyridin-4-yl)pyrimidin-4-yl) amino)tetrahydro-2H-thiopyran-4-carbonitrile 1,1-dioxide;

1-((2-(1H-pyrrolo[2,3-b]pyridin-3-yl)pyrimidin-4-yl) amino)cyclobutane-3-carbonitrile;

1-((2-(7H-pyrrolo[2,3-d]pyrimidin-4-yl)pyrimidin-4-yl) amino)cyclobutane-3-carbonitrile;

1-((2-(1H-pyrrolo[2,3-b]pyridin-4-yl)pyrimidin-4-yl) amino)cyclobutanecarbonitrile;

1-((2-(1H-pyrrolo[2,3-b]pyridin-3-yl)pyrimidin-4-yl) amino)cyclopentanecarbonitrile;

1-((2-(7H-pyrrolo[2,3-d]pyrimidin-4-yl)pyrimidin-4-yl) amino)cyclopentanecarbonitrile;

1-((2-(1H-pyrrolo[2,3-b]pyridin-4-yl)pyrimidin-4-yl) amino)cyclopentanecarbonitrile;

(R)-2-((2-(1H-pyrrolo[2,3-b]pyridin-3-yl)pyrimidin-4-yl) amino-2-methylbutanenitrile;

(R)-2-((2-(7H-pyrrolo[2,3-d]pyrimidin-4-yl)pyrimidin-4-yl)amino-2-methylbutanenitrile;

(R)-2-((2-(1H-pyrrolo[2,3-b]pyridin-4-yl)pyrimidin-4-yl) amino-2-methylbutanenitrile;

and isomers, solvates, or pharmaceutically acceptable salts thereof.

Terminology

The term "alkyl" refers to a straight or branched alkyl group having from 1 to 12 carbon atoms in the chain, and examples of the alkyl group include methyl (Me), ethyl (Et), n-propyl, isopropyl, butyl, isobutyl, sec-butyl, tert-butyl (t-Bu), pentyl, isopentyl, tert-pentyl, hexyl, isohexyl, and any group which is considered to be equivalent to the above examples according to those of ordinary skill in the art and the teachings provided herein.

The term "alkoxy" refers to an alkyl group as defined above which is bonded to an oxygen atom. The alkoxy group is attached to the parent structure via the oxygen atom.

The term "amino" refers to a —NH$_2$ group or a mono- or di-alkylamino group.

The term cycloalkyl refers to a saturated and partially saturated, monocyclic, fused polycyclic, bridged polycyclic, or spiro polycyclic carbocyclic ring having from 3 to 12 ring atoms per ring. Illustrative examples of cycloalkyl groups include the following moieties in suitable bonding form:

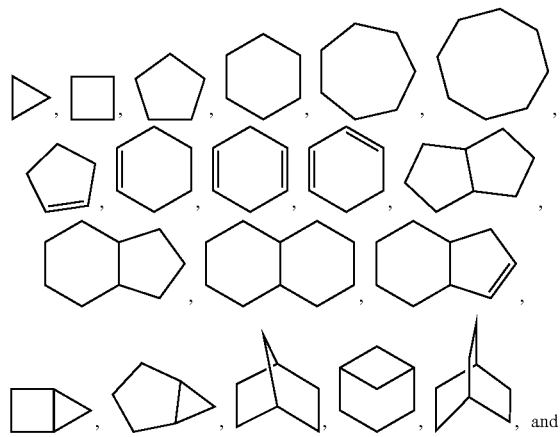

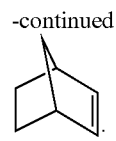

The term "aryl" refers to a 5-6 membered carbo-aromatic ring, such as benzene; bicyclic rings wherein at least one of the rings is a carbo-aromatic ring such as naphthalene, anthracene and 1,2,3,4-tetrahydroquinoline; and tricyclic rings wherein at least one of the rings is a carbo-aromatic ring, such as fluorene.

For example, an aryl group includes a 5-6 membered carbo-aromatic ring fused with a 5-7 membered heterocyclic ring including one or more heteroatoms selected from the group consisting of nitrogen, oxygen, and sulfur, provided that the point of attachment is on the carbo-aromatic ring. A divalent radical is formed by a substituted benzene derivative and a free valence state of the atom on the ring, which is designated as a substituted phenylene radical. A divalent free radical is derived from a monovalent polycyclic hydrocarbon free radical whose name ends with a "radical" by reducing a free valence hydrogen atom, the name being the addition of "ene" after the corresponding monovalent free radical. For example, a naphthyl group having two points of attachment is referred to as a naphthylene group. However, the aryl group does not contain, nor does it overlap in any way with the heterocyclic aryl groups respectively defined below. Thus, as defined herein, if one or more carboaromatic rings are attached with a heteroaromatic ring, the resulting ring system is an aromatic heterocyclic group rather than an aryl group.

The term "aromatic heterocyclic group" refers to:

a 5-8 membered monocyclic aromatic hydrocarbon containing one or more heteroatoms selected from N, O and S, such as from 1 to 4 heteroatoms, and in some embodiments, from 1 to 3 heteroatoms, wherein the other atoms in the ring are carbon atoms;

a 8-12 membered bicyclic aromatic hydrocarbon containing one or more heteroatoms selected from N, O and S, such as from 1 to 4 heteroatoms, and in some embodiments, from 1 to 3 heteroatoms, wherein the other atoms in the ring are carbon atoms and at least one ring is an aromatic ring; and

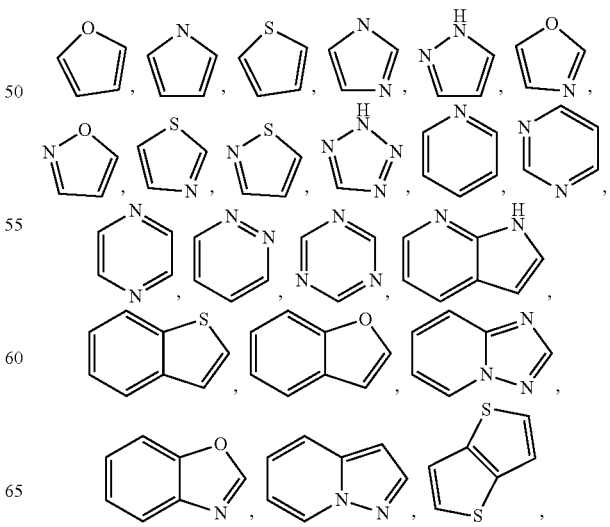

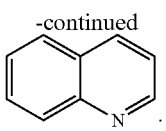

The term "heterocycloalkyl" refers to a saturated or partially unsaturated, monocyclic or polycyclic, cyclic hydrocarbon group comprising from 3 to 20 ring atoms wherein one or more ring atoms are selected from hetero atoms selected from nitrogen, oxygen or S(O)m (where m is an integer from 0 to 2), and the remaining ring atoms are carbon. Preferably, 3 to 12 ring atoms are included, of which 1 to 4 are heteroatoms. More preferably, a heterocycloalkyl ring contains from 3 to 10 ring atoms, and more preferably, a heterocycloalkyl ring contains from 5 to 6 ring atoms. Non-limiting examples of monocyclic heterocycloalkyl groups include pyrrolidinyl, piperidinyl, morpholinyl, tetrahydrofuranyl and the like. Polycyclic heterocycloalkyl groups include spiro, fused, and bridged heterocycloalkyl groups. The heterocyclic ring may be substituted or unsubstituted, and when substituted, the substituent is preferably one or more of the following groups independently selected from alkyl, haloalkyl, alkoxy, alkylamino, halogen, hydroxyl, amino, oxo, alkylamino, cycloalkyl, heterocycloalkyl, heterocycloalkoxy, hydroxyalkyl, carboxy or carboxylate.

The term "halogen" means chlorine, fluorine, bromine or iodine. The term "halo" means chloro, fluoro, bromo or iodo. The term "haloalkyl" refers to an alkyl group as defined above which is substituted by one or more halogen atoms.

The term "haloalkoxy" refers to an alkoxy group as defined above which is substituted by one or more halogen atoms.

The term "acyl" refers to a R—C(O)— group of a straight, branched, or cyclic configuration or a combination thereof having 1 to 10 carbon atoms, which is attached to the parent structure through a hydroxy function group. Such group may be saturated or unsaturated, and aliphatic or aromatic.

In the embodiments provided herein, if the compound disclosed herein contains a basic group, it can form a salt with an acid, and a salt of a pyrimidine derivative can be produced by a method well known to those skilled in the art.

Common acid salts include organic acid salts, inorganic acid salts, and the like. In general, the commonly used organic acid salts are citrate, fumarate, oxalate, malate, lactate, sulfonate (e.g., camphor sulfonate, p-toluenesulfonate, methanesulfonate, and the like), etc.; inorganic acid salts include hydrohalides, sulfates, phosphates, nitrates, and the like.

For example, a lower alkylsulfonic acid such as methanesulfonic acid, trifluoromethanesulfonic acid or the like may form a mesylate salt, a triflate salt; and an arylsulfonic acid such as benzenesulfonic acid, p-toluenesulfonic acid or the like may form p-toluenesulfonate, benzenesulfonate; an organic carboxylic acid such as acetic acid, fumaric acid, tartaric acid, oxalic acid, maleic acid, malic acid, succinic acid, citric acid or the like may form corresponding salts; an amino acid such as glutamic acid or aspartic acid can form glutamate or aspartate. An inorganic acid such as hydrohalic acids (such as hydrofluoric acid, hydrobromic acid, hydroiodic acid, hydrochloric acid), nitric acid, carbonic acid, sulfuric acid or phosphoric acid or the like may also form corresponding salts.

In an embodiment provided herein, if the compound disclosed herein contains an acidic group, it can form a salt with a base. The salt of the compound disclosed herein can be prepared by a method well known to those skilled in the art. For example, it can form a salt with an alkali metal such as sodium, potassium or lithium; with an alkaline earth metal such as calcium or barium; with other metals such as magnesium or aluminum; and can also form a salt with an organic base such as dicyclohexylamine, guanidine or triethylamine.

In a second aspect, provided herein is a medicament which utilizes the JAK inhibitor compound of the formula (I), an isomer or a pharmaceutically acceptable salt or a solvate thereof as an active ingredient. The above medicament may further comprise one or more pharmaceutically acceptable carriers, including conventional diluents, excipients, fillers, binders, wetting agents, disintegrants, absorption promoters, surfactants, adsorption carriers, lubricants, etc. in the pharmaceutical field. If necessary, flavoring agents, sweeteners or the like may be added. The medicament disclosed herein can be prepared into various forms such as tablets, powders, granules, capsules, oral liquids and injectable preparations, and the medicaments in the above various dosage forms can be prepared according to a conventional method in the pharmaceutical field.

In a third aspect, provided herein are a heterocyclic compound of formula (I) as a JAK inhibitor, an isomer and a pharmaceutically acceptable salt thereof for use in the manufacture of a medicament for the treatment of autoimmune diseases, rheumatoid arthritis, skin conditions, multiple sclerosis, psoriatic arthritis, inflammatory bowel disease, myasthenia gravis, psoriasis in human or animal, especially for the treatment of JAK kinase-related diseases.

The inventors of the present disclosure have confirmed by experiments that some compounds disclosed herein have a good inhibitory effect on JAK kinase, especially JAK1, and has low inhibitory activity on JAK2, JAK3, suggesting that this product is a selective JAK inhibitor. A medicament using a compound of the formula (I) or a pharmaceutically acceptable salt thereof has lower toxicity for the treatment of autoimmune diseases, rheumatoid arthritis, skin conditions, multiple sclerosis, rheumatoid arthritis, psoriatic arthritis, inflammatory bowel disease, myasthenia gravis, and psoriasis.

DETAILED DESCRIPTION OF THE SPECIFIC EMBODIMENTS

The practicability of the present disclosure are described below by way of examples, and those skilled in the art will understand that modifications or substitutions of the corresponding technical features are still within the scope of the claimed invention.

Example 1

2-(3-(4-(1H-pyrrolo[2,3-b]pyridin-3-yl)-1H-pyrazol-1-yl)-1-(ethylsulfonyl)azetidin-3-yl)acetonitrile

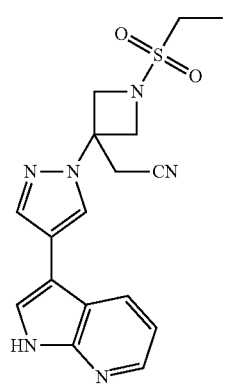 [SMILES: CCS(=O)(=O)N1CC(CC#N)(n2cc(-c3c[nH]c4ncccc34)cn2)C1]

Step 1

3-(1-(1-ethoxyethyl)-1H-pyrazol-4-yl)-1-((2-trimethylsilyl)ethoxy)methyl)-1H-pyrrolo[2,3-b]pyridine

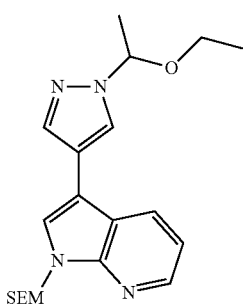 [SMILES: CCOC(C)n1cc(-c2cn(COCC[Si](C)(C)C)c3ncccc23)cn1]

2.7 g of 3-bromo-1-((2-(trimethylsilyl)ethoxy)methyl)-1H-pyrrolo[2,3-b]pyridine, 3.2 g of 1-(1-ethoxyethyl)-4-(4,4,5,5-tetramethyl-1,3,2-dioxaborolan-2-yl)-1H-pyrazole, 3 g of potassium carbonate, and 90 mg of Pd(dppf)Cl$_2$ were dissolved in 21 ml of n-butanol and 7 ml of water, heated to 100° C. for 20 hours. The reaction was completed. The reaction solution was concentrated to dryness, and extracted with ethyl acetate. The organic layer was dried over anhydrous sodium sulfate, filtered, concentrated, and purified by silica gel column chromatography to give 1.2 g of an oil.

Step 2

3-(1H-pyrazol-4-yl)-1-((2-trimethylsilyl)ethoxy)methyl)-1H-pyrrolo[2,3-b]pyridine

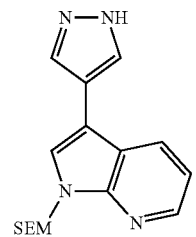 [SMILES: C[Si](C)(C)CCOCn1cc(-c2cn[nH]c2)c2cccnc21]

1.2 g of the product of step 1 was added to 9 ml of tetrahydrofuran and 22.5 ml of H$_2$O. 3 ml of 10% dilute hydrochloric acid was then added to the mixture, and stirred at room temperature. The reaction was completed after 1 hour. 30% sodium hydroxide was added to adjust the pH to 7. The mixture was extracted with dichloromethane, dried (Na$_2$SO$_4$) and concentrated to give 1.0 g of oil.

Step 3

2-(1-(ethylsulfonyl)-3-(4-(1-((2-trimethylsilyl)ethoxy)methyl)-1H-pyrrolo[2,3-b]pyridin-3-yl)-1H-pyrazol-1-yl)-azetidin-3-yl)acetonitrile

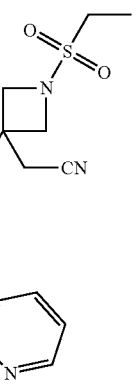

0.5 g of the product of step 2 and 0.2 g of 2-(1-(ethylsulfonyl)azetidin-3-ylidene)acetonitrile were added to 20 ml of acetonitrile. 10 mg of DBU was added to the reaction at room temperature and reacted for 5 hours. After the reaction was completed, the mixture was extracted with ethyl acetate, and washed with water. The organic layer was dried, filtered, concentrated, and purified by column chromatography to give 0.6 g of the object product.

Step 4

2-(3-(4-(1H-pyrrolo[2,3-b]pyridin-3-yl)-1H-pyrazol-1-yl)-1-(ethylsulfonyl) azetidin-3-yl)acetonitrile To 0.5 g of the product of step 3 was added 5 ml of trifluoroacetic acid, and reacted at room temperature for 3 h. After the reaction was completed (thin layer chromatography (ethyl acetate/petroleum ether 1:2)), the mixture was concentrated to dryness. 1 ml of ethylenediamine was added to the residue and reacted for 2 h. The mixture was concentrated to dryness, filtered, concentrated, and purified by column chromatography to give the object product (0.3 g).

$^1$HNMR (400 MHz, DMSO-D6) δ 11.74 (s, 1H), 8.51 (s, 1H), 8.33 (d, J=7.9 Hz, 1H), 8.26 (d, J=4.6 Hz, 1H), 8.09 (s, 1H), 7.80 (d, J=1.8 Hz, 1H), 7.15 (dd, J=7.9, 4.7 Hz, 1H), 4.55 (d, J=8.8 Hz, 2H), 4.22 (d, J=8.8 Hz, 2H), 3.64 (s, 2H), 3.25 (q, J=7.3 Hz, 2H), 1.25 (t, J=7.3 Hz, 3H).

MS (ESI): 367.14 (M+1)

Example 2

2-(4-(4-(1H-pyrrolo[2,3-b]pyridin-3-yl)-1H-pyrazol-1-yl)-1,1-dioxotetrahydro-2H-thiopyran-4-yl)acetonitrile

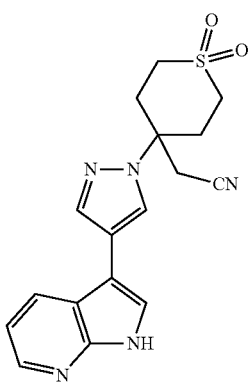 [SMILES: N#CCC1(n2cc(-c3c[nH]c4ncccc34)cn2)CCS(=O)(=O)CC1]

The synthesis was carried out by referring to the method of Example 1.

$^1$HNMR (400 MHz, DMSO-D6) δ 11.72 (s, 1H), 8.50 (s, 1H), 8.36-8.31 (m, 1H), 8.26 (dd, 1H), 8.06 (s, 1H), 7.79 (d, 1H), 7.14 (dd, 1H), 3.29 (d, 4H), 3.13-2.96 (m, 4H), 2.55 (d, 2H).

MS (ESI): 356.11 (M+1)

Example 3

2-(4-(4-(7H-pyrrolo[2,3-d]pyrimidin-4-yl)-1H-pyrazol-1-yl)-1,1-dioxotetrahydro-2H-thiopyran-4-yl)acetonitrile

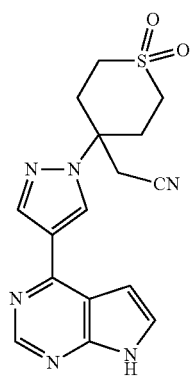 [SMILES: N#CCC1(n2cc(-c3ncnc4[nH]ccc34)cn2)CCS(=O)(=O)CC1]

The synthesis was carried out by referring to the method of Example 1.

Alternatively, the synthesis was carried out according to the following steps:

Step 1

2-(1,1-dioxo-4-(4-(7-((2-(trimethylsilyl))ethoxy)methyl)-7H-pyrrolo[2,3-d]pyrimidin-4-yl)-1H-pyrazol-1-yl)-tetrahydro-2H-thiopyran-4-yl)acetonitrile

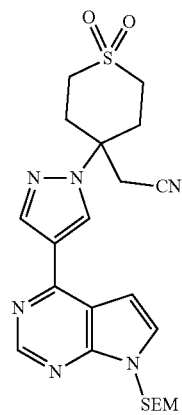 [SMILES: C[Si](C)(C)CCOCn1ccc2c(-c3cnn(C4(CC#N)CCS(=O)(=O)CC4)c3)ncnc21]

In a 250 ml round bottom flask, 15 g of 4-(1H-pyrazol-4-yl)-7 (trimethylsilyl)ethoxy)methyl)-7H-pyrrolo[2,3-d]pyrimidine and 100 ml of acetonitrile were added at room temperature under nitrogen protection, and cooled to 0° C. in an ice bath. 0.72 g of DBU and 9.0 g of 2-(1,1-dioxodihydro-2H-thiopyran-4(3H)-ylidene)acetonitrile were then added, continued to react at 0° C. for 5 hours, and then reacted at room temperature of 20° C. overnight, until the raw materials were basically consumed. The reaction was monitored by thin layer chromatography. The solid was filtered and washed with ethyl acetate. The filtrate was concentrated to dryness. The solid was precipitated by adding ethyl acetate and then washed with ethyl acetate/n-hexane to give a solid. The solids were combined and dried to give 8 g of the product.

Step 2

2-(4-(4-(7H-pyrrolo[2,3-d]pyrimidin-4-yl)-1H-pyrazol-1-yl)-1,1-dioxotetrahydro-2H-thiopyran-4-yl)acetonitrile 5 g of the product of step 1 was added to 30 ml of trifluoroacetic acid, and reacted at room temperature for 3 h. After the reaction was completed (thin layer chromatography (ethyl acetate/petroleum ether 1:2)), the mixture was concentrated to dryness. 1 ml of ethylenediamine was added and reacted for 2 h. The mixture was concentrated to dry, filtered, concentrated, and purified by column chromatography to give 2.6 g of the object product.

¹HNMR (400 MHz, DMSO-D6) δ 12.15 (s, 1H), 8.91 (s, 1H), 8.71 (s, 1H), 8.47 (s, 1H), 7.62 (m, 1H), 7.10 (m, 1H), 3.41 (s, 2H), 3.29 (m, 2H), 3.00-3.17 (m, 4H), 2.54-2.60 (m, 2H).

MS (ESI): 356.11 (M+1)

Example 4

2-(4-(4-(1H-pyrrolo[2,3-b]pyridin-4-yl)-1H-pyrazol-1-yl)-1,1-dioxotetrahydro-2H-thiopyran-4-yl)acetonitrile

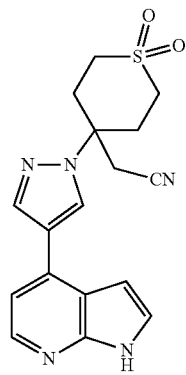 [SMILES: N#CCC1(n2cc(-c3ccnc4[nH]ccc34)cn2)CCS(=O)(=O)CC1]

The synthesis was carried out by referring to the method of Example 1.

¹HNMR (400 MHz, DMSO-D6) δ 11.72 (s, 1H), 8.78 (s, 1H), 8.33 (s, 1H), 8.20 (d, 1H), 7.53 (d, 1H), 7.36 (d, 1H), 6.90 (d, 1H), 3.38 (s, 2H), 3.28-3.33 (m, 2H), 3.12 (m, 2H), 3.02 (m, 2H), 2.56 (m, 2H).

MS (ESI): 356.11 (M+1)

Example 5

2-(4-(4-(1H-pyrrolo[2,3-b]pyridin-3-yl)-1H-pyrazol-1-yl)-1-(methylsulfonyl)piperidin-4-yl)-N-(2,2,2-trifluoroethyl)acetonitrile

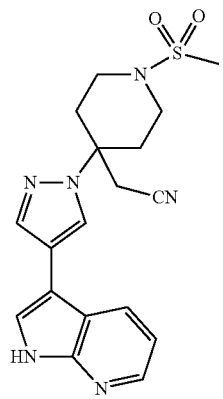 [SMILES: CS(=O)(=O)N1CCC(CC#N)(n2cc(-c3c[nH]c4ncccc34)cn2)CC1]

The synthesis was carried out by referring to the method of Example 1.

MS (ESI): 385.14 (M+1)

Example 6

2-(3-(4-(1H-pyrrolo[2,3-b]pyridin-3-yl)-1H-pyrazol-1-yl)-1-(ethylsulfonyl)azetidin-3-yl)acetamide

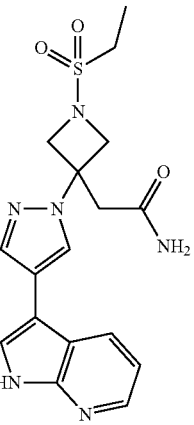

0.3 g of the product of Example (1) and 10 ml of methanol were added to 2 ml of 1 M sodium hydroxide, and reacted at 50° C. for 2 hours. The pH was adjusted to 7 with hydrochloric acid, methanol was removed, and filtered to afford the object product.

¹HNMR (400 MHz, DMSO-D6) δ 11.70 (s, 1H), 8.33-8.23 (m, 3H), 7.99 (s, 1H), 7.74 (d, J=2.5 Hz, 1H), 7.47 (s, 1H), 7.12 (dd, J=7.9, 4.7 Hz, 1H), 6.97 (s, 1H), 4.46 (d, J=8.9 Hz, 2H), 4.35 (d, J=8.9 Hz, 2H), 3.20 (q, J=7.1 Hz, 2H), 3.08 (s, 2H), 1.24 (t, J=7.3 Hz, 3H).

MS (ESI): 389.14 (M+1)

Example 7

2-(3-(4-(1H-pyrrolo[2,3-b]pyridin-3-yl)-1H-pyrazol-1-yl)-1-(ethylsulfonyl) azetidin-3-yl)-N-(2,2,2-trifluoroethyl)acetamide

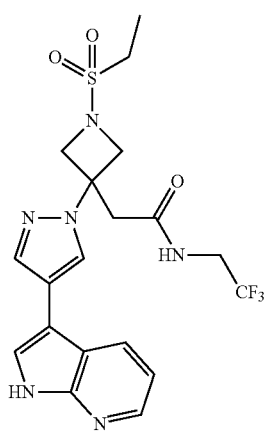 [SMILES: CCS(=O)(=O)N1CC(CC(=O)NCC(F)(F)F)(n2cc(-c3c[nH]c4ncccc34)cn2)C1]

Step 1

2-(3-(4-H-pyrrolo[2,3-b]pyridin-3-yl)-1H-pyrazol-1-yl)-1-(ethylsulfonyl)azetidin-3-yl)acetic acid

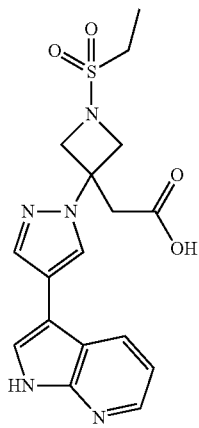 [SMILES: CCS(=O)(=O)N1CC(CC(=O)O)(n2cc(-c3c[nH]c4ncccc34)cn2)C1]

To 0.6 g of the product of the example (1) was added 4 ml of 1 M sodium hydroxide and 20 ml of methanol, and was reacted under reflux for 10 hours. The pH was adjusted to 6 with hydrochloric acid and the methanol was removed. The mixture was extracted with dichloromethane, dried, concentrated, and filtered to give 0.4 g of the object product.

Step 2

2-(3-(4-(1H-pyrrolo[2,3-b]pyridin-3-yl)-1H-pyrazol-1-yl)-1-(ethylsulfonyl)azetidin-3-yl)-N-(2,2,2-trifluoroethyl)acetamide 0.4 g of the product of step 1 was dissolved in 5 ml of dry DMF, and 0.18 g of N-(3-dimethylaminopropyl)-N'-ethyl-carbodiimide hydrochloride (EDC.HCl) was added. After stirring for 1 hour, 0.1 g of trifluoroethylamine was added. After 2 hours of reaction, the mixture was diluted with water, extracted with dichloromethane, dried, concentrated, and then purified by column chromatography to give 0.3 g of the object product.

$^1$H NMR (400 MHz, DMSO-D6) δ 11.68 (s, 1H), 8.76 (m, 1H), 8.24-8.28 (m, 3H), 7.78 (s, 1H), 7.12 (m, 1H), 4.47 (d, 2H), 4.35 (d, 2H), 3.83 (m, 2H), 3.20 (m, 4H), 1.24 (t, 3H).

MS (ESI): 471.14 (M+1)

Example 8

2-(3-(4-(1H-pyrrolo[2,3-d]pyrimidin-4-yl)-1H-pyrazol-1-yl)-1-(ethylsulfonyl) azetidin-3-yl)-N-(2,2,2-trifluoroethyl)acetamide

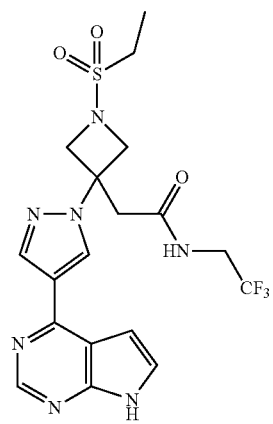 [SMILES: CCS(=O)(=O)N1CC(CC(=O)NCC(F)(F)F)(n2cc(-c3ncnc4[nH]ccc34)cn2)C1]

It was prepared by referring to the method of step 2 of Example 7.

$^1$H NMR (400 MHz, DMSO-D6) δ 11.12 (s, 1H), 8.73 (m, 1H), 8.71 (m, 1H), 8.68 (m, 1H), 8.39 (s, 1H), 7.59 (d, 1H), 7.02 (d, 1H), 4.53 (d, 2H), 4.36 (d, 2H), 3.81 (m, 2H), 3.27 (s, 2H), 3.18-3.23 (m, 2H), 1.23 (t, 3H).

MS (ESI): 472.13 (M+1)

Example 9

2-(3-(4-(1H-pyrrolo[2,3-b]pyridin-4-yl)-1H-pyrazol-1-yl)-1-(ethylsulfonyl)azetidin-3-yl)-N-(2,2,2-trifluoroethyl)acetamide

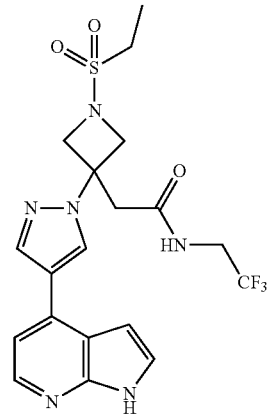 [SMILES: CCS(=O)(=O)N1CC(CC(=O)NCC(F)(F)F)(n2cc(-c3ccnc4[nH]ccc34)cn2)C1]

It was prepared by referring to the method of step 2 of Example 7.

MS (ESI): 471.14 (M+1)

Example 10

2-(3-(4-(1H-pyrrolo[2,3-b]pyridin-4-yl)-1H-pyrazol-1-yl)-1-(ethylsulfonyl)azetidin-3-yl)-N-methylacetamide

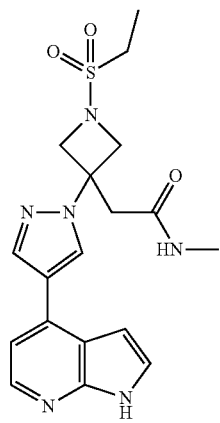 [SMILES: CCS(=O)(=O)N1CC(CC(=O)NC)(n2cc(-c3ccnc4[nH]ccc34)cn2)C1]

It was prepared by referring to the method of step 2 of Example 7.

MS (ESI): 403.15 (M+1)

Example 11

2-(3-(4-(1H-pyrrolo[2,3-b]pyridin-4-yl)-1H-pyrazol-1-yl)-1-(ethylsulfonyl)azetidin-3-yl)acetamide

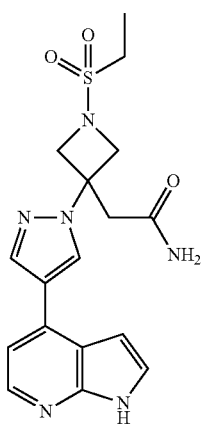 [SMILES: CCS(=O)(=O)N1CC(CC(N)=O)(n2cc(-c3ccnc4[nH]ccc34)cn2)C1]

It was prepared by referring to the method of Example 6.

$^1$HNMR (400 MHz, DMSO-D6) δ 11.72 (s, 1H), 8.52 (s, 1H), 8.21 (s, 1H), 8.14 (d, J=5.0 Hz, 1H), 7.46 (dd, J=8.5, 5.4 Hz, 2H), 7.27 (d, J=5.0 Hz, 1H), 6.94 (s, 1H), 7.79 (dd, J=3.5, 1.8 Hz, 1H), 3.64 (s, 2H), 4.47 (d, J=9.0 Hz, 2H), 4.32 (d, J=9.0 Hz, 2H), 3.17 (q, J=7.3 Hz, 2H), 3.08 (s, 2H), 1.20 (t, J=7.3 Hz, 3H).

MS (ESI): 389.14 (M+1)

Example 12

2-(3-(4-(7H-pyrrolo[2,3-d]pyrimidin-4-yl)-1H-pyrazol-1-yl)-1-(methylsulfonyl) azetidin-3-yl)-N-(2,2,2-trifluoroethyl)acetamide

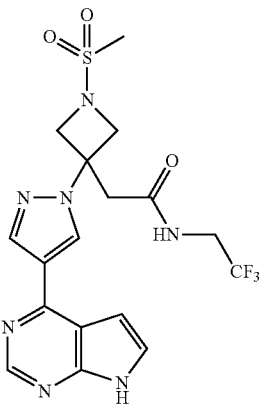 [SMILES: CS(=O)(=O)N1CC(CC(=O)NCC(F)(F)F)(n2cc(-c3ncnc4[nH]ccc34)cn2)C1]

It was prepared by referring to the method of step 2 of Example 7.

MS (ESI): 458.12 (M+1)

Example 13

2-(3-(4-(7H-pyrrolo[2,3-d]pyrimidin-4-yl)-1H-pyrazol-1-yl)-1-(methylsulfonyl)azetidin-3-yl)-N-methylacetamide

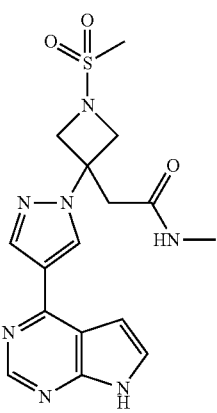 [SMILES: CNC(=O)CC1(n2cc(-c3ncnc4[nH]ccc34)cn2)CN(S(C)(=O)=O)C1]

It was prepared by referring to the method of step 2 of Example 7.

MS (ESI): 390.13 (M+1)

Example 14

2-(3-(4-(7H-pyrrolo[2,3-d]pyrimidin-4-yl)-1H-pyrazol-1-yl)-1-(methylsulfonyl)azetidin-3-yl) acetamide

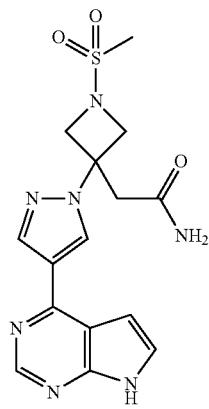 [SMILES: CS(=O)(=O)N1CC(CC(N)=O)(n2cc(-c3ncnc4[nH]ccc34)cn2)C1]

It was prepared by referring to the method of Example 6.
MS (ESI): 376.11 (M+1)

Example 15

2-(3-(4-(1H-pyrrolo[2,3-b]pyridin-4-yl)-1H-pyrazol-1-yl)-1-(methylsulfonyl)azetidin-3-yl)-N-(2,2,2-trifluoroethyl)acetamide

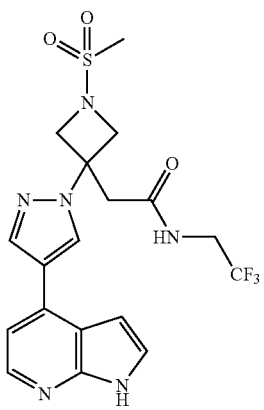 [SMILES: CS(=O)(=O)N1CC(CC(=O)NCC(F)(F)F)(n2cc(-c3ccnc4[nH]ccc34)cn2)C1]

It was prepared by referring to the method of step 2 of Example 7.
MS (ESI): 457.12 (M+1)

Example 16

2-(3-(4-(1H-pyrrolo[2,3-b]pyridin-4-yl)-1H-pyrazol-1-yl)-1-(methylsulfonyl)azetidin-3-yl)-N-methylacetamide

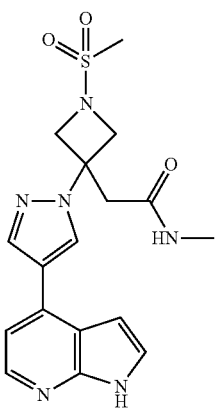 [SMILES: CNC(=O)CC1(n2cc(-c3ccnc4[nH]ccc34)cn2)CN(S(C)(=O)=O)C1]

It was prepared by referring to the method of step 2 of Example 7.
MS (ESI): 389.14 (M+1)

Example 17

2-(3-(4-(1H-pyrrolo[2,3-b]pyridin-4-yl)-1H-pyrazol-1-yl)-1-(methylsulfonyl)azetidin-3-yl)acetamide

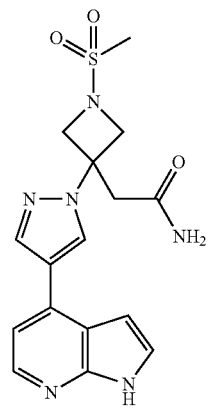 [SMILES: CS(=O)(=O)N1CC(CC(N)=O)(n2cc(-c3ccnc4[nH]ccc34)cn2)C1]

It was prepared by referring to the method of Example 6.
MS (ESI): 375.12 (M+1)

Example 18

2-(4-(4-(1H-pyrrolo[2,3-b]pyridin-3-yl)-1H-pyrazol-1-yl)-1,1-dioxotetrahydro-2H-thiopyran-4-yl)acetamide

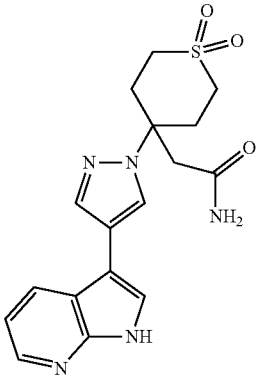 [SMILES: NC(=O)CC1(n2cc(-c3c[nH]c4ncccc34)cn2)CCS(=O)(=O)CC1]

It was prepared by referring to the method of Example 6.

$^1$HNMR (400 MHz, DMSO-D6) δ 11.67 (s, 1H), 8.37-8.27 (m, 2H), 8.25 (dd, J=4.6 Hz, 1.4 Hz, 1H), 7.98 (s, 1H), 7.75 (d, J=2.5 Hz, 1H), 7.31 (s, 1H), 7.12 (dd, J=7.9, 4.7 Hz, 1H), 6.91 (s, 1H), 3.21 (d, J=13.2 Hz, 2H), 2.55 (d, J=11.9 Hz, 2H), 3.08 (d, J=14.7 Hz, 2H), 3.08 (t, J=13.4 Hz, 2H), 2.95 (t, J=13.4 Hz, 2H), 2.69 (t, J=12.5 Hz, 2H), 2.61 (s, 2H).

MS (ESI): 374.12 (M+1)

Example 19

2-(4-(4-(1H-pyrrolo[2,3-b]pyridin-3-yl)-1H-pyrazol-1-yl)-1,1-dioxotetrahydro-2H-thiopyran-4-yl)-N-(2,2,2-trifluoroethyl)acetamide

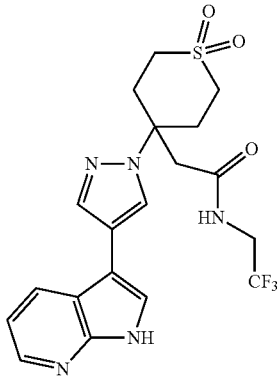 [SMILES: O=C(CC1(n2cc(-c3c[nH]c4ncccc34)cn2)CCS(=O)(=O)CC1)NCC(F)(F)F]

It was prepared by referring to the method of step 2 of Example 7.

$^1$HNMR (400 MHz, DMSO-D6) δ 11.68 (s, 1H), 8.61 (m, 1H), 8.28-8.32 (m, 2H), 8.24-8.25 (m, 1H), 7.98 (s, 1H), 7.74 (d, 1H), 7.12 (m, 1H), 3.82 (m, 2H), 2.65-3.34 (m, 8H), 2.50 (m, 2H).

MS (ESI): 456.13 (M+1)

Example 20

2-(4-(4-(7H-pyrrolo[2,3-d]pyrimidin-4-yl)-1H-pyrazol-1-yl)-1,1-dioxotetrahydro-2H-thiopyran-4-yl)-N-(2,2,2-trifluoroethyl)acetamide

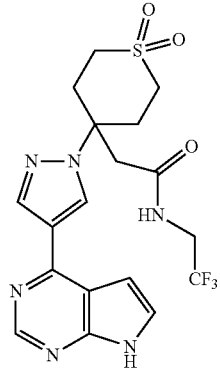 [SMILES: O=C(CC1(n2cc(-c3ncnc4[nH]ccc34)cn2)CCS(=O)(=O)CC1)NCC(F)(F)F]

It was prepared by referring to the method of step 2 of Example 7.

$^1$HNMR (400 MHz, DMSO-D6) δ 12.11 (s, 1H), 8.72 (s, 1H), 8.67 (s, 1H), 8.59 (m, 1H), 8.39 (s, 1H), 7.59 (d, 1H), 7.05 (d, 1H), 3.81 (m, 2H), 3.24 (m, 2H), 3.12 (m, 2H), 2.97 (m, 2H), 2.83 (s, 2H), 2.67 (m, 2H).

MS (ESI): 457.12 (M+1)

Example 21

2-(4-(4-(7H-pyrrolo[2,3-b]pyridin-4-yl)-1H-pyrazol-1-yl)-1,1-dioxotetrahydro-2H-thiopyran-4-yl)-N-(2,2,2-trifluoroethyl)acetamide

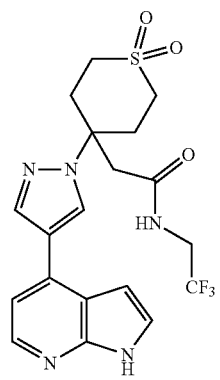 [SMILES: O=C(CC1(n2cc(-c3ccnc4[nH]ccc34)cn2)CCS(=O)(=O)CC1)NCC(F)(F)F]

It was prepared by referring to the method of step 2 of Example 7.

MS (ESI): 456.12 (M+1)

Example 22

2-(4-(4-(7H-pyrrolo[2,3-b]pyridin-3-yl)-1H-pyrazol-1-yl)-1-(methylsulfonyl)piperidin-4-yl)-N-(2,2,2-trifluoroethyl)acetamide

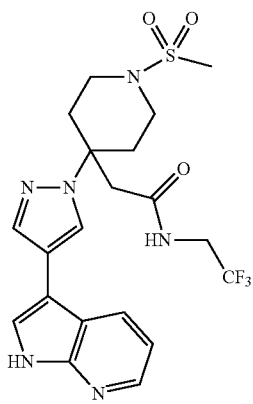 [SMILES: CS(=O)(=O)N1CCC(CC(=O)NCC(F)(F)F)(n2cc(-c3c[nH]c4ncccc34)cn2)CC1]

It was prepared by referring to the method of step 2 of Example 7.

MS (ESI): 485.15 (M+1)

Example 23

2-(4-(4-(7H-pyrrolo[2,3-b]pyrimidin-4-yl)-1H-pyrazol-1-yl)-1-(methylsulfonyl)piperidin-4-yl)-N-(2,2,2-trifluoroethyl)acetamide

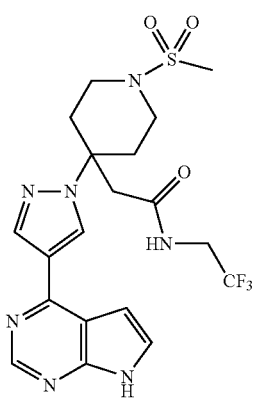 [SMILES: CS(=O)(=O)N1CCC(CC(=O)NCC(F)(F)F)(n2cc(-c3ncnc4[nH]ccc34)cn2)CC1]

It was prepared by referring to the method of step 2 of Example 7.

MS (ESI): 486.15 (M+1)

Example 24

2-(4-(4-(7H-pyrrolo[2,3-b]pyridin-4-yl)-1H-pyrazol-1-yl)-1-(methylsulfonyl)piperidin-4-yl)-N-(2,2,2-trifluoroethyl)acetamide

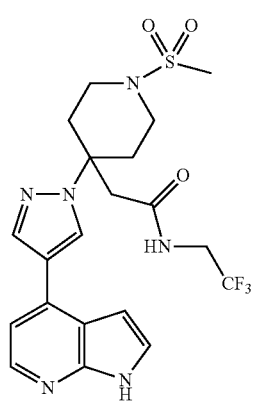 [SMILES: CS(=O)(=O)N1CCC(CC(=O)NCC(F)(F)F)(n2cc(-c3ccnc4[nH]ccc34)cn2)CC1]

It was prepared by referring to the method of step 2 of Example 7.

MS (ESI): 485.15 (M+1)

Example 25

2-(1-(4-(1H-pyrrolo[2,3-b]pyridin-3-yl)-1H-pyrazol-1-yl)cyclopentyl)-N-(2,2,2-trifluoroethyl) acetamide

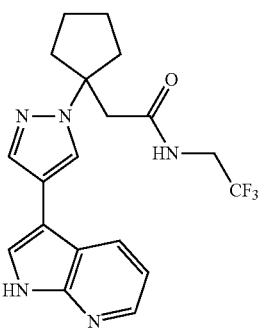 [SMILES: O=C(CC1(n2cc(-c3c[nH]c4ncccc34)cn2)CCCC1)NCC(F)(F)F]

It was prepared by referring to the method of step 2 of Example 7.

$^1$HNMR (400 MHz, DMSO-D6) δ 11.60 (s, 1H), 8.42 (m, 1H), 8.22 (m, 2H), 8.10 (s, 1H), 7.84 (s, 1H), 7.66 (d, 1H), 7.10 (m, 1H), 3.79 (m, 2H), 2.86 (s, 2H), 2.50 (m, 2H), 2.07 (m, 2H), 1.71 (m, 2H), 1.58 (m, 2H).

MS (ESI): 485.15 (M+1)

Example 26

2-(1-(4-(1H-pyrrolo[2,3-b]pyrimidin-4-yl)-1H-pyrazol-1-yl)cyclopentyl)-N-(2,2,2-trifluoroethyl)acetamide

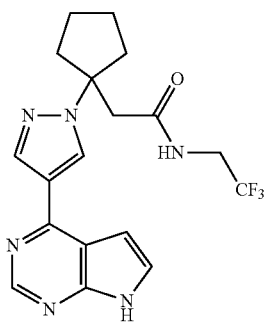 [SMILES: O=C(CC1(n2cc(-c3ncnc4[nH]ccc34)cn2)CCCC1)NCC(F)(F)F]

It was prepared by referring to the method of step 2 of Example 7.
MS (ESI): 485.15 (M+1)

Example 27

2-(1-(4-(1H-pyrrolo[2,3-b]pyridin-4-yl)-1H-pyrazol-1-yl)cyclopentyl)-N-(2,2,2-trifluoroethyl) acetamide

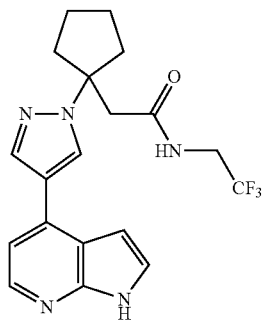 [SMILES: O=C(CC1(n2cc(-c3ccnc4[nH]ccc34)cn2)CCCC1)NCC(F)(F)F]

It was prepared by referring to the method of step 2 of Example 7.
MS (ESI): 392.17 (M+1)

Example 28

3-(4-(1H-pyrrolo[2,3-b]pyridin-3-yl)-1H-pyrazol-1-yl)-3-methyl-N-(2,2,2-trifluoroethyl)butanamide

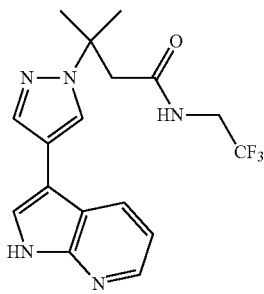 [SMILES: CC(C)(CC(=O)NCC(F)(F)F)n1cc(-c2c[nH]c3ncccc23)cn1]

It was prepared by referring to the method of step 2 of Example 7.
MS (ESI): 366.15 (M+1)

Example 29

3-(4-(7H-pyrrolo[2,3-b]pyrimidin-4-yl)-1H-pyrazol-1-yl)-3-methyl-N-(2,2,2-trifluoroethyl)butanamide

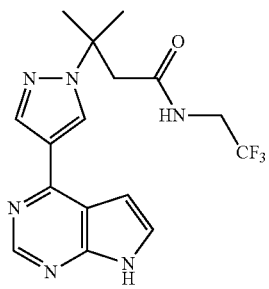 [SMILES: CC(C)(CC(=O)NCC(F)(F)F)n1cc(-c2ncnc3[nH]ccc23)cn1]

It was prepared by referring to the method of step 2 of Example 7.
MS (ESI): 367.14 (M+1)

Example 30

3-(4-(7H-pyrrolo[2,3-b]pyridin-4-yl)-1H-pyrazol-1-yl)-3-methyl-N-(2,2,2-trifluoroethyl)butanamide

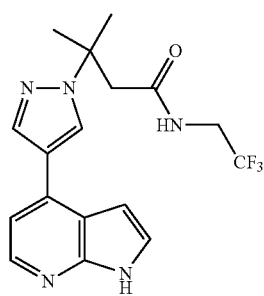 [SMILES: CC(C)(CC(=O)NCC(F)(F)F)n1cc(-c2ccnc3[nH]ccc23)cn1]

It was prepared by referring to the method of step 2 of Example 7.
MS (ESI): 367.14 (M+1)

Example 31

3-((2-(1H-pyrrolo[2,3-b]pyridin-3-yl)pyrimidin-4-yl) amino)-1-(methylsulfonyl)-N-(2,2,2-trifluoroethyl) azetidin-3-carboxamide

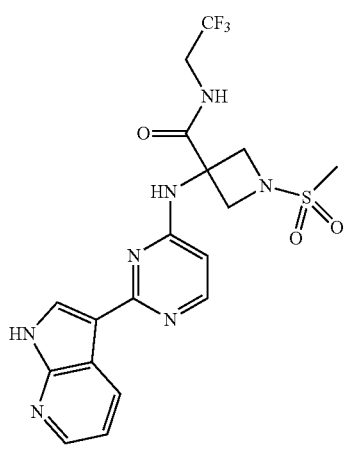 [SMILES: CS(=O)(=O)N1CC(Nc2ccnc(-c3c[nH]c4ncccc34)n2)(C(=O)NCC(F)(F)F)C1]

Step 1. Methyl 3-((2-chloropyrimidin-4-yl)amino)-1-(methylsulfonyl)azetidin-3-carboxylate

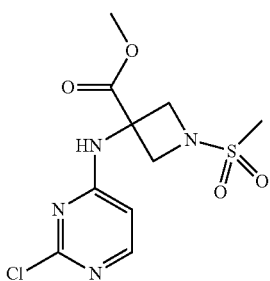 [SMILES: COC(=O)C1(Nc2ccnc(Cl)n2)CN(S(C)(=O)=O)C1]

3.3 g of 2,4-dichloropyrimidine and 5 g of methyl 3-amino-1-(methylsulfonyl)azetidin-3-carboxylate were dissolved in 50 ml of tetrahydrofuran. 5 ml of DIPEA was added and reacted at 40° C. for 3 hours. The mixture was diluted with water, extracted with dichloromethane, dried, filtered, concentrated, and purified by column chromatography to give 6 g of the object product.

Step 2

3-((2-chloropyrimidin-4-yl)amino)-1-(methylsulfonyl) azetidin-3-carboxylic acid

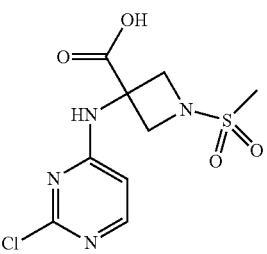 [SMILES: CS(=O)(=O)N1CC(Nc2ccnc(Cl)n2)(C(=O)O)C1]

2 g of the product of step 1 was dissolved in 10 ml. 4 ml of 2M potassium hydroxide was added, and the reaction was stirred at room temperature for 2 hours. The solvent was removed, and hydrochloric acid was added to adjust the pH to 6. The mixture was filtered and dried to give 1.6 g of the object product.

Step 3

1-(methylsulfonyl)-3-((2-(1-p-toluenesulfonyl-1H-pyrrolo[2,3-b]pyridin-3-yl)pyrimidin-4-yl)amino) azetidine-3-carboxylic acid

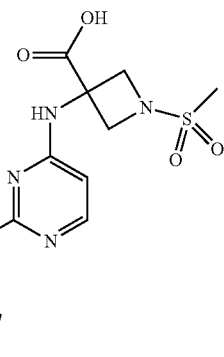

In 24 ml of dioxane/water (5:1), 2 g of the product of step 2, 1.26 g of 3-(4,4,5,5-tetramethyl-1,3,2-dioxolan-2-yl)-1-p-toluenesulfonyl-1H-pyrrolo[2,3-b]pyridine, 1.0 g of potassium carbonate, and 0.1 g of Pd(dppf)Cl$_2$ were added and heated to 90° C. and reacted for 3 h. The mixture was adjusted to pH 6 with hydrochloric acid and filtered. The filtrate was subjected to reduced pressure to remove dioxane, diluted with water, extracted with ethyl acetate, dried, concentrated and purified by column chromatography to give 1.8 g of the object product.

Step 4

3-((2-(1H-pyrrolo[2,3-b]pyridin-3-yl)pyrimidin-4-yl)amino)-1-(methylsulfonyl)azetidin-3-carboxylic acid

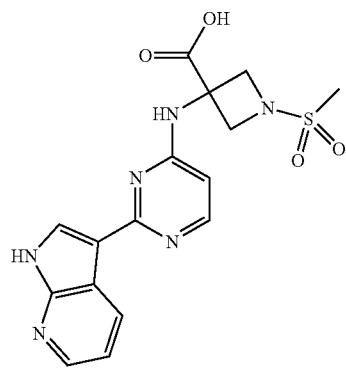 [SMILES: CS(=O)(=O)N1CC(Nc2ccnc(-c3c[nH]c4ncccc34)n2)(C(=O)O)C1]

To 0.8 g of the product of step 3 was added 3 ml of 2M potassium hydroxide and 10 ml of methanol, and refluxed for 2 hours. The solvent was removed, and the pH was adjusted to 6 with hydrochloric acid and filtered to give 0.5 g of the target product.

Step 5

3-((2-(1H-pyrrolo[2,3-b]pyridin-3-yl)pyrimidin-4-yl)amino)-1-(methylsulfonyl)-N-(2,2,2-trifluoroethyl)azetidin-3-carboxamide 0.3 g of the product of step 4 was dissolved in 5 ml of dry DMF. 0.16 g of N-(3-dimethylaminopropyl)-N'-ethylcarbodiimide hydrochloride (EDC.HCl) was added and stirred for 2 hours. 0.098 g of 2,2,2-trifluoroethylamine was then added, and reacted for 1 hour. After the reaction was completed, the mixture was diluted with water, extracted with dichloromethane, dried, concentrated and purified by column chromatography to give 0.2 g of the target product.
MS (ESI): 470.12 (M+1)

Example 32

3-((2-(1H-pyrrolo[2,3-b]pyridin-3-yl)pyrimidin-4-yl)amino)-1-(ethylsulfonyl)-N-(2,2,2-trifluoroethyl)azetidin-3-carboxamide

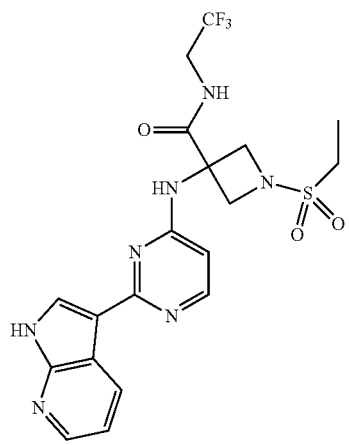 [SMILES: CCS(=O)(=O)N1CC(Nc2ccnc(-c3c[nH]c4ncccc34)n2)(C(=O)NCC(F)(F)F)C1]

It was prepared by referring to the method of Example 31.
MS (ESI): 484.13 (M+1)

Example 33

3-((2-(1H-pyrrolo[2,3-b]pyridin-3-yl)pyrimidin-4-yl)amino)-1-(cyclopropylsulfonyl)-N-(2,2,2-trifluoroethyl)azetidin-3-carboxamide

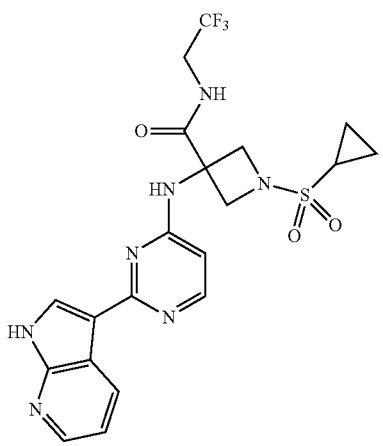 [SMILES: O=C(NCC(F)(F)F)C1(Nc2ccnc(-c3c[nH]c4ncccc34)n2)CN(S(=O)(=O)C2CC2)C1]

It was prepared by referring to the method of Example 31.
MS (ESI): 496.13 (M+1)

Example 34

3-(5-fluoro-2-(1H-pyrrolo[2,3-b]pyridin-3-yl)py-rimidin-4-yl)amino)-1-(methylsulfonyl)-N-(2,2,2-trifluoroethyl)azetidin-3-carboxamide

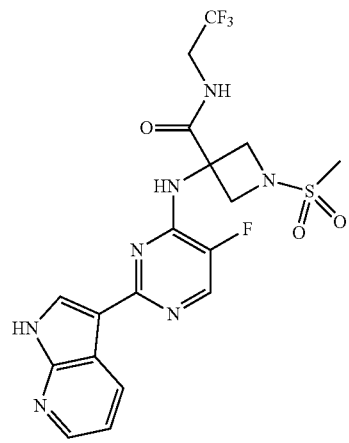 [SMILES: CS(=O)(=O)N1CC(Nc2nc(-c3c[nH]c4ncccc34)ncc2F)(C(=O)NCC(F)(F)F)C1]

It was prepared by referring to the method of Example 31.
MS (ESI): 488.10 (M+1)

Example 36

3-(5-fluoro-2-(1H-pyrrolo[2,3-b]pyridin-3-yl)py-rimidin-4-yl)amino)-1-(cyclopropylsulfonyl)-N-(2,2,2-trifluoroethyl)azetidin-3-carboxamide

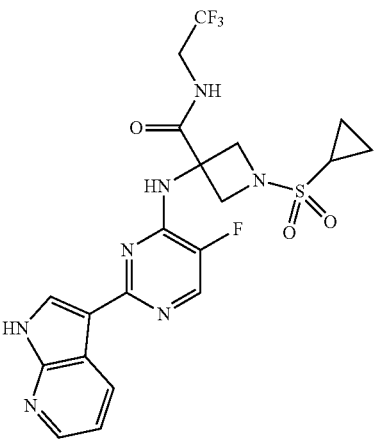

It was prepared by referring to the method of Example 31.
MS (ESI): 514.12 (M+1)

Example 35

3-(5-fluoro-2-(1H-pyrrolo[2,3-b]pyridin-3-yl)py-rimidin-4-yl)amino)-1-(ethylsulfonyl)-N-(2,2,2-trif-luoroethyl) azetidin-3-carboxamide

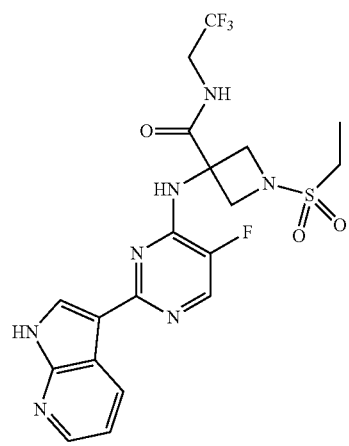 [SMILES: CCS(=O)(=O)N1CC(Nc2nc(-c3c[nH]c4ncccc34)ncc2F)(C(=O)NCC(F)(F)F)C1]

It was prepared by referring to the method of Example 31.
MS (ESI): 502.12 (M+1)

Example 37

4-((2-(1H-pyrrolo[2,3-b]pyridin-3-yl)pyrimidin-4-yl)amino)-1-(methylsulfonyl)-N-(2,2,2-trifluoroethyl)piperidin-4-carboxamide

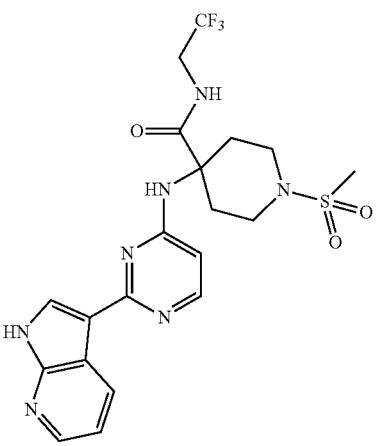 [SMILES: CS(=O)(=O)N1CCC(Nc2ccnc(-c3c[nH]c4ncccc34)n2)(C(=O)NCC(F)(F)F)CC1]

It was prepared by referring to the method of Example 31.
MS (ESI): 498.15 (M+1)

Example 38

4-((2-(1H-pyrrolo[2,3-b]pyridin-3-yl)pyrimidin-4-yl)amino)-1-(ethylsulfonyl)-N-(2,2,2-trifluoroethyl)piperidin-4-carboxamide

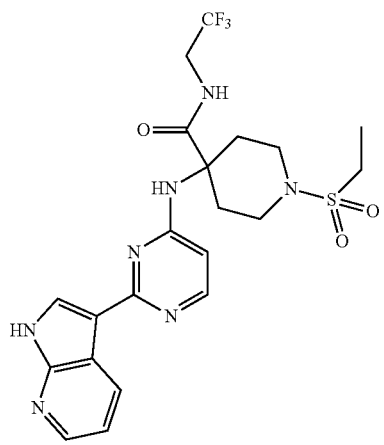 [SMILES: CCS(=O)(=O)N1CCC(Nc2ccnc(-c3c[nH]c4ncccc34)n2)(C(=O)NCC(F)(F)F)CC1]

It was prepared by referring to the method of Example 31.
MS (ESI): 412.16 (M+1)

Example 40

4-((5-fluoro-2-(1H-pyrrolo[2,3-b]pyridin-3-yl)pyrimidin-4-yl)amino)-1-(methylsulfonyl)-N-(2,2,2-trifluoroethyl)piperidin-4-carboxamide

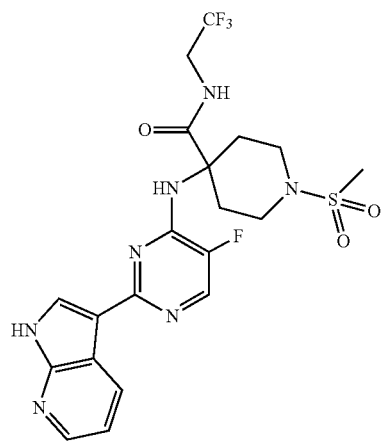

It was prepared by referring to the method of Example 31.
MS (ESI): 516.16 (M+1)

Example 39

4-((2-(1H-pyrrolo[2,3-b]pyridin-3-yl)pyrimidin-4-yl)amino)-1-(cyclopropylsulfonyl)-N-(2,2,2-trifluoroethyl)piperidin-4-carboxamide

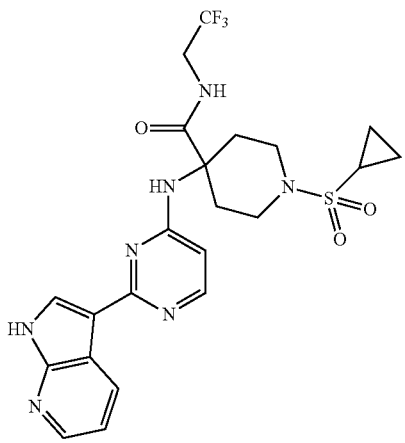 [SMILES: O=C(NCC(F)(F)F)C1(Nc2ccnc(-c3c[nH]c4ncccc34)n2)CCN(S(=O)(=O)C2CC2)CC1]

It was prepared by referring to the method of Example 31.
MS (ESI): 524.16 (M+1)

Example 41

4-((5-fluoro-2-(1H-pyrrolo[2,3-b]pyridin-3-yl)pyrimidin-4-yl)amino)-1-(ethylsulfonyl)-N-(2,2,2-trifluoroethyl)piperidin-4-carboxamide

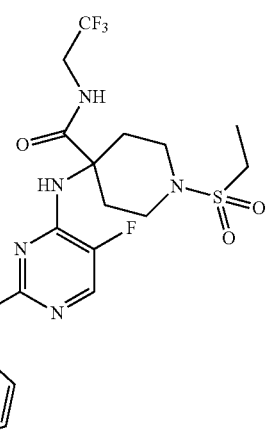

It was prepared by referring to the method of Example 31.
MS (ESI): 530.16 (M+1)

Example 42

4-((5-fluoro-2-(1H-pyrrolo[2,3-b]pyridin-3-yl)pyrimidin-4-yl)amino)-1-(cyclopropylsulfonyl)-N-(2,2,2-trifluoroethyl)piperidin-4-carboxamide

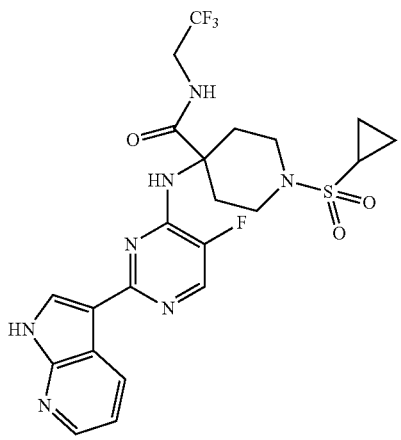 [SMILES: O=C(NCC(F)(F)F)C1(Nc2nc(-c3c[nH]c4ncccc34)ncc2F)CCN(S(=O)(=O)C2CC2)CC1]

It was prepared by referring to the method of Example 31.
MS (ESI): 542.16 (M+1)

Example 43

4-((2-(1H-pyrrolo[2,3-b]pyridin-3-yl)pyrimidin-4-yl)amino)-N-(2,2,2-trifluoroethyl)tetrahydro-2H-thiopyran-4-carboxamide 1,1-dioxide

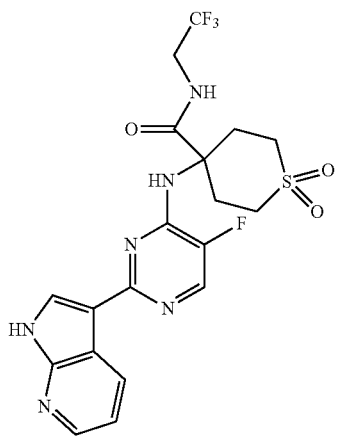 [SMILES: O=C(NCC(F)(F)F)C1(Nc2nc(-c3c[nH]c4ncccc34)ncc2F)CCS(=O)(=O)CC1]

It was prepared by referring to the method of Example 31.
MS (ESI): 469.12 (M+1)

Example 44

4-((5-fluoro-2-(1H-pyrrolo[2,3-b]pyridin-3-yl)pyrimidin-4-yl)amino)-N-(2,2,2-trifluoroethyl)tetrahydro-2H-thiopyran-4-carboxamide 1,1-dioxide

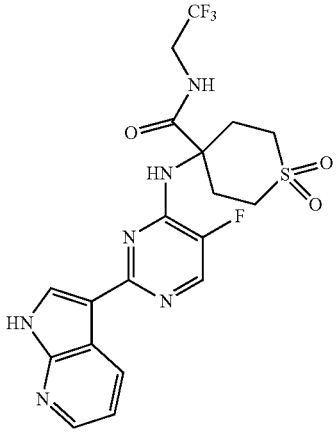 [SMILES: O=C(NCC(F)(F)F)C1(Nc2nc(-c3c[nH]c4ncccc34)ncc2F)CCS(=O)(=O)CC1]

It was prepared by referring to the method of Example 31.
MS (ESI): 487.11 (M+1)

Example 45

3-((2-(1H-pyrrolo[2,3-b]pyridin-3-yl)pyrimidin-4-yl)amino)-1-(ethylsulfonyl) azetidine-3-carbonitrile

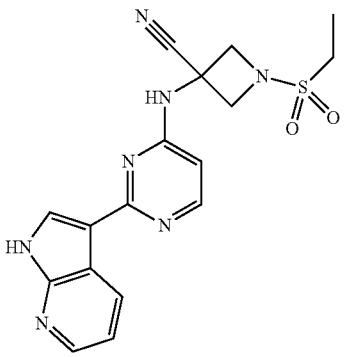 [SMILES: CCS(=O)(=O)N1CC(C#N)(Nc2ccnc(-c3c[nH]c4ncccc34)n2)C1]

It was prepared by referring to the method of Example 31.
MS (ESI): 384.12 (M+1)

Example 46

3-((2-(7H-pyrrolo[2,3-d]pyrimidin-4-yl)pyrimidin-4-yl)amino)-1-(ethylsulfonyl)azetidine-3-carbonitrile

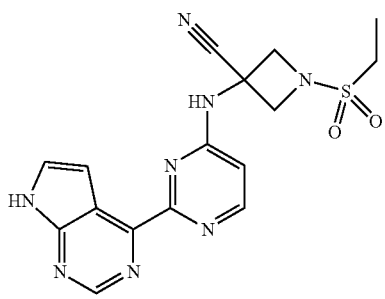 [SMILES: CCS(=O)(=O)N1CC(C#N)(Nc2ccnc(-c3ncnc4[nH]ccc34)n2)C1]

It was prepared by referring to the method of Example 31.
MS (ESI): 385.12 (M+1)

Example 47

3-((2-(1H-pyrrolo[2,3-b]pyridin-4-yl)pyrimidin-4-yl)amino)-1-(ethylsulfonyl)azetidine-3-carbonitrile

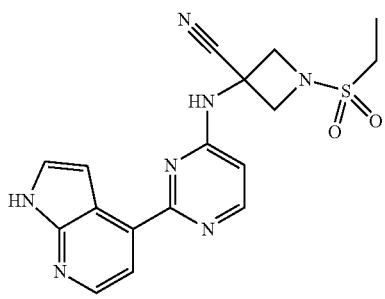 [SMILES: CCS(=O)(=O)N1CC(C#N)(Nc2ccnc(-c3ccnc4[nH]ccc34)n2)C1]

It was prepared by referring to the method of Example 31.
MS (ESI): 385.12 (M+1)

Example 48

3-((2-(1H-pyrrolo[2,3-b]pyridin-3-yl)pyrimidin-4-yl)amino)-1-(methylsulfonyl) azetidine-3-carbonitrile

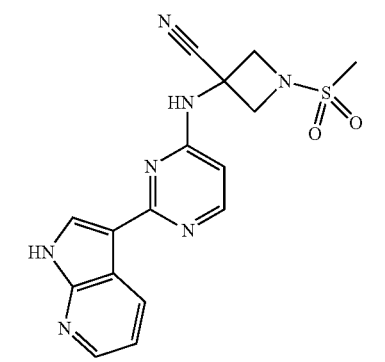 [SMILES: CS(=O)(=O)N1CC(C#N)(Nc2ccnc(-c3c[nH]c4ncccc34)n2)C1]

It was prepared by referring to the method of Example 31.
MS (ESI): 370.1 (M+1)

Example 49

3-((2-(7H-pyrrolo[2,3-d]pyrimidin-4-yl)pyrimidin-4-yl)amino)-1-(methylsulfonyl) azetidine-3-carbonitrile

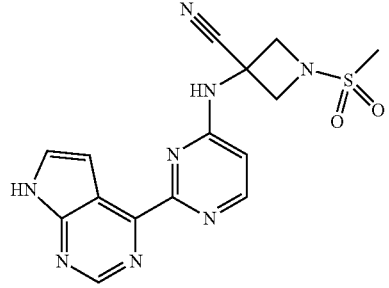 [SMILES: CS(=O)(=O)N1CC(C#N)(Nc2ccnc(-c3ncnc4[nH]ccc34)n2)C1]

It was prepared by referring to the method of Example 32.
MS (ESI): 371.1 (M+1)

Example 50

3-((2-(1H-pyrrolo[2,3-b]pyridin-4-yl)pyrimidin-4-yl)amino)-1-(methylsulfonyl) azetidine-3-carbonitrile

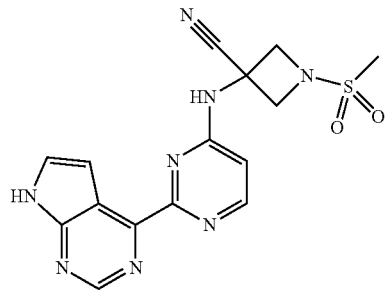 [SMILES: CS(=O)(=O)N1CC(C#N)(Nc2ccnc(-c3ncnc4[nH]ccc34)n2)C1]

It was prepared by referring to the method of Example 31.
MS (ESI): 370.1 (M+1)

Example 51

4-((2-(1H-pyrrolo[2,3-b]pyridin-3-yl)pyrimidin-4-yl)amino)tetrahydro-2H-thiopyran-4-carbonitrile 1,1-dioxide

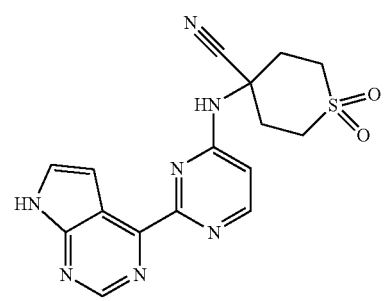 [SMILES: N#CC1(Nc2ccnc(-c3ncnc4[nH]ccc34)n2)CCS(=O)(=O)CC1]

It was prepared by referring to the method of Example 31.
MS (ESI): 369.1 (M+1)

Example 52

4-((2-(7H-pyrrolo[2,3-d]pyrimidin-4-yl)pyrimidin-4-yl)amino)tetrahydro-2H-thiopyran-4-carbonitrile 1,1-dioxide

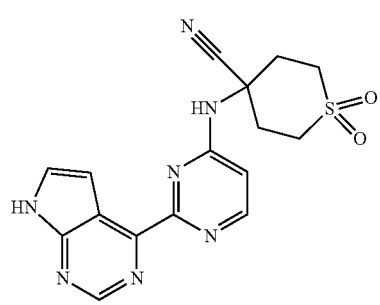 [SMILES: N#CC1(Nc2ccnc(-c3ncnc4[nH]ccc34)n2)CCS(=O)(=O)CC1]

It was prepared by referring to the method of Example 31.
MS (ESI): 370.1 (M+1)

Example 53

4-((2-(1H-pyrrolo[2,3-b]pyridin-4-yl)pyrimidin-4-yl)amino)tetrahydro-2H-thiopyran-4-carbo nitrile 1,1-dioxide

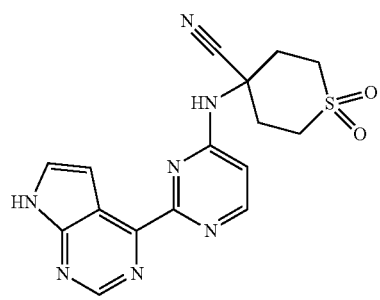 [SMILES: N#CC1(Nc2ccnc(-c3ncnc4[nH]ccc34)n2)CCS(=O)(=O)CC1]

It was prepared by referring to the method of Example 31.
MS (ESI): 369.1 (M+1)

Example 54

1-((2-(1H-pyrrolo[2,3-b]pyridin-3-yl)pyrimidin-4-yl)amino)cyclobutane-3-carbonitrile

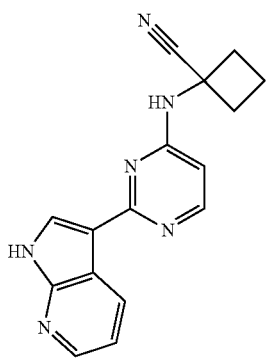 [SMILES: N#CC1(Nc2ccnc(-c3c[nH]c4ncccc34)n2)CCC1]

It was prepared by referring to the method of Example 31.
MS (ESI): 291.13 (M+1)

Example 55

1-((2-(7H-pyrrolo[2,3-d]pyrimidin-4-yl)pyrimidin-4-yl)amino)cyclobutane-3-carbonitrile

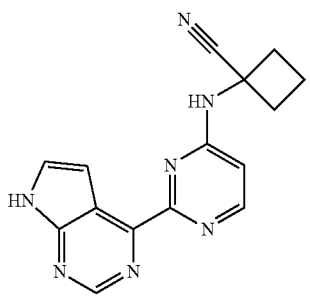 [SMILES: N#CC1(Nc2ccnc(-c3ncnc4[nH]ccc34)n2)CCC1]

It was prepared by referring to the method of Example 31.
MS (ESI): 292.13 (M+1)

Example 56

1-((2-(1H-pyrrolo[2,3-b]pyridin-4-yl)pyrimidin-4-yl)amino)cyclobutanecarbonitrile

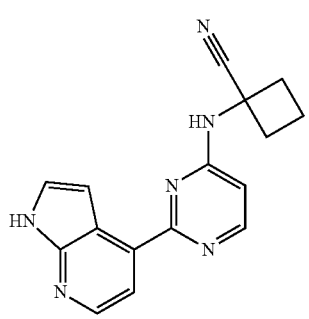 [SMILES: N#CC1(Nc2ccnc(-c3ccnc4[nH]ccc34)n2)CCC1]

47

It was prepared by referring to the method of Example 31.
MS (ESI): 291.13 (M+1)

Example 57

1-((2-(1H-pyrrolo[2,3-b]pyridin-3-yl)pyrimidin-4-yl)amino)cyclopentanecarbonitrile

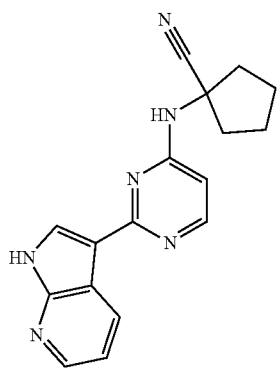 [SMILES: N#CC1(Nc2ccnc(-c3c[nH]c4ncccc34)n2)CCCC1]

It was prepared by referring to the method of Example 31.
MS (ESI): 305.15 (M+1)

Example 58

1-((2-(7H-pyrrolo[2,3-d]pyrimidin-4-yl)pyrimidin-4-yl)amino)cyclopentanecarbonitrile

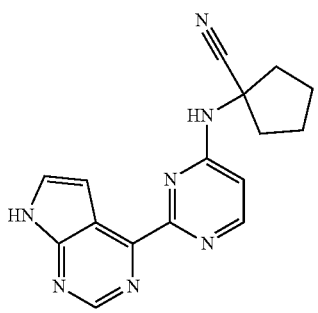 [SMILES: N#CC1(Nc2ccnc(-c3ncnc4[nH]ccc34)n2)CCCC1]

It was prepared by referring to the method of Example 31.
MS (ESI): 306.14 (M+1)

48

Example 59

1-((2-(1H-pyrrolo[2,3-b]pyridin-4-yl)pyrimidin-4-yl)amino)cyclopentanecarbonitrile

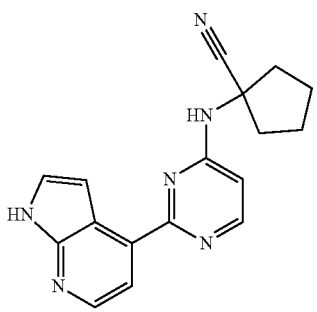 [SMILES: N#CC1(Nc2ccnc(-c3ccnc4[nH]ccc34)n2)CCCC1]

It was prepared by referring to the method of Example 31.
MS (ESI): 305.14 (M+1)

Example 60

(R)-2-((2-(1H-pyrrolo[2,3-b]pyridin-3-yl)pyrimidin-4-yl)amino-2-methylbutanenitrile

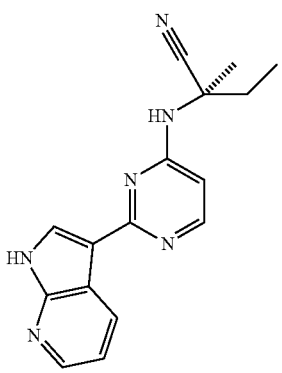 [SMILES: CC[C@](C)(C#N)Nc1ccnc(-c2c[nH]c3ncccc23)n1]

It was prepared by referring to the method of Example 31.
MS (ESI): 293.14 (M+1)

Example 61

(R)-2-((2-(7H-pyrrolo[2,3-d]pyrimidin-4-yl)pyrimidin-4-yl)amino-2-methylbutanenitrile

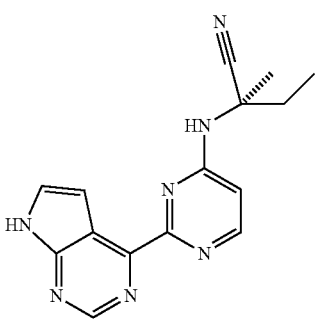 [SMILES: CC[C@](C)(C#N)Nc1ccnc(-c2ncnc3[nH]ccc23)n1]

It was prepared by referring to the method of Example 31.
MS (ESI): 294.15 (M+1)

Example 62

(R)-2-((2-(1H-pyrrolo[2,3-b]pyridin-4-yl)pyrimidin-4-yl)amino-2-methylbutanenitrile

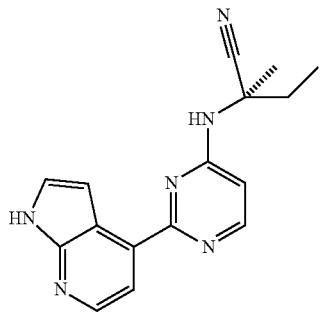 [SMILES: CC[C@](C)(C#N)Nc1ccnc(-c2ccnc3[nH]ccc23)n1]

It was prepared by referring to the method of Example 31.
MS (ESI): 293.15 (M+1)

Example 63. Inhibition of JAK

The study of the effect of compounds on the activity of purified recombinant JAK was performed by studying the inhibitory activity of the compounds on JAK from the enzymatic level. The experimental principle is to use a luminescence kinase assay to detect the ADP content produced by the reaction of JAK with the substrate Poly (4:1 Glu, Tyr) peptide: after ADP is converted to ATP, ATP can act as a substrate for the Ultra-Glo luciferase catalytic reaction, producing an optical signal. The luminescence signal is positively correlated with the amount of ADP and kinase activity. Therefore, the inhibitory effect of the compounds on the recombinant JAK was determined by observing the luminescence signal produced by the reaction of JAK and the substrate, and was expressed by $IC_{50}$.

Experimental method: 10 different concentrations of compounds were incubated with JAK1, JAK2 and JAK3, respectively, for 60 minutes at 37° C. The substrate and ATP were then added, mixed, and reacted at 37° C. for 50 minutes. 25 μl of ADP-Glo™ was added and mixed for 2 minutes. The reaction was carried out for 50 minutes at room temperature. Further, 50 μl of the detection reagent was added and mixed for 2 minutes, and incubated at room temperature for 50 minutes, and detected by a chemiluminometer. The results are shown in Table 1.

TABLE 1

Experimental results of inhibition of JAK by the compounds disclosed herein

| Compound | Inhibition of JAK1 $IC_{50}$(nM) | Inhibition of JAK2 $IC_{50}$(nM) | Inhibition of JAK3 $IC_{50}$(nM) |
| --- | --- | --- | --- |
| Example 1 compound | a | b | c |
| Example 2 compound | a | b | c |
| Example 3 compound | a | b | a |
| Example 4 compound | a | a | c |
| Example 5 compound | a | b | a |
| Example 6 compound | c | c | c |
| Example 7 compound | c | c | c |
| Example 8 compound | c | c | c |
| Example 9 compound | c | c | c |
| Example 10 compound | c | c | c |
| Example 11 compound | c | c | c |
| Example 12 compound | b | b | c |
| Example 13 compound | c | c | c |
| Example 14 compound | b | b | c |
| Example 15 compound | a | b | a |
| Example 18 compound | a | c | a |
| Example 19 compound | b | c | c |
| Example 20 compound | b | c | c |
| Example 21 compound | b | c | c |
| Example 22 compound | c | c | c |
| Example 23 compound | b | c | c |
| Example 24 compound | b | c | c |
| Example 25 compound | b | c | b |
| Example 26 compound | b | c | c |
| Example 27 compound | b | c | c |
| Example 28 compound | c | b | c |
| Example 29 compound | c | b | a |
| Example 31 compound | c | c | b |
| Example 32 compound | c | c | b |
| Example 33 compound | c | c | b |
| Example 34 compound | c | c | b |
| Example 36 compound | c | c | b |
| Example 37 compound | c | c | b |
| Example 38 compound | c | c | b |
| Example 39 compound | c | c | b |
| Example 42 compound | c | b | b |
| Example 44 compound | c | b | b |
| Example 45 compound | c | b | b |
| Example 46 compound | c | c | c |
| Example 47 compound | c | c | b |

TABLE 1-continued

Experimental results of inhibition of JAK by the compounds disclosed herein

| Compound | Inhibition of JAK1 IC$_{50}$(nM) | Inhibition of JAK2 IC$_{50}$(nM) | Inhibition of JAK3 IC$_{50}$(nM) |
|---|---|---|---|
| Example 48 compound | c | c | c |
| Example 49 compound | c | c | b |
| Example 50 compound | c | c | c |
| Example 51 compound | c | c | b |
| Example 52 compound | c | c | c |
| Example 53 compound | c | c | b |
| Example 54 compound | c | c | b |
| Example 55 compound | c | c | c |
| Example 56 compound | c | c | c |
| Example 57 compound | c | c | b |
| Example 58 compound | c | c | c |
| Example 59 compound | c | c | b |
| Example 60 compound | c | c | b |
| Example 61 compound | c | c | c |
| Example 62 compound | c | c | c |

Note:
1. (a) ≤20 nM;
2. (b) >20 nM to 50 nM;
3. (c) >50 nM

As an example, Example 3 was compared with the results of the existing JAK inhibitor under the same experimental conditions, and the results are shown in Table 2.

TABLE 2

Comparison of the inhibitory effects of the compound disclosed herein and the existing JAK inhibitors on JAK

| Compound | Inhibition of JAK1 IC$_{50}$(nM) | Inhibition of JAK2 IC$_{50}$(nM) | Inhibition of JAK3 IC$_{50}$(nM) |
|---|---|---|---|
| Example 3 compound | 10.5 | 22.0 | 19.0 |
| Tofacitinib | 20-50 | 20-50 | <20 |
| Ruxolitinib* | 3.3 | 2.8 | 390 |
| Baricitinib* | 5.9 | 5.5 | >400 |

Note:
The test results of Ruxolitinib* and Baricitinib* were obtained from FDA's new drug application.

The results showed that the compound of Example 3 had high inhibitory activity against JAK1 and low inhibitory activity against JAK2, suggesting that the selectivity of the compound for JAK1 is higher than that of Baricitinib and Ruxolitinib (the compound disclosed in CN101448826A), and the latter two positive drugs are not selective for JAK1 and JAK2.

Example 64. Effect of Repeated Administration of the Compound Disclosed Herein on Hematological Parameters in Rats 48 healthy Wistar rats were taken, half ♀ and half ♂. According to the body weight, they were randomly divided into the control group (Veh). The compound of Example 3 was administered by gavage at doses of 1.5 mg·kg$^{-1}$·d$^{-1}$ and 4.5 mg·kg$^{-1}$·d$^{-1}$. Ruxolitinib was administered by gavage at dose of 4.5 mg·kg$^{-1}$·d$^{-1}$. There were 12 rats in each group, half ♀ and half ♂. The drug was administered by gavage once a day for 4 weeks, and the hematological parameters were examined 1 day and 2 days after the last administration. RESULTS: After the end of administration, for the groups of the gavage administration of the compound of Example 3 at doses of 1.5 mg·kg$^{-1}$·d$^{-1}$ and 4.5 mg·kg$^{-1}$·d$^{-1}$, there was no significant decrease in the value of the animal hematological parameter WBC compared with the control group (Veh) ($P<0.05$); for the group of Luxolitinib (the compound disclosed in CN101448826A) at dose of 4.5 mg·kg$^{-1}$·d$^{-1}$, there was significant decrease in the value of the animal hematological parameter WBC compared with the control group (Veh) ($P<0.05$), suggesting that the compounds disclosed herein have less side effects when treating rheumatoid arthritis.

The results showed that the compound of Example 3 had high inhibitory activity against JAK1 and low inhibitory activity against JAK2, suggesting that the selectivity of the compound for JAK1 is higher than that of Baricitinib and Ruxolitinib (the compound disclosed in CN101448826A), and the latter two positive drugs are not selective for JAK1 and JAK2.

What is claimed is:
1. A compound of Formula (I):

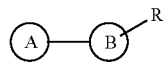

Formula (I)

and an isomer, a solvate, or a pharmaceutically acceptable salt thereof,

Ⓑ is selected from:

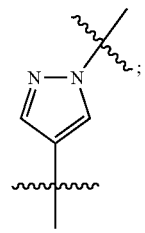 [SMILES: *c1cnn(*)c1]

R is selected from:

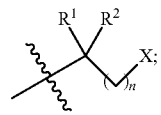

when X is —CONH—R$^4$, R$^4$ is hydrogen, C$_1$-C$_6$ alkyl, or C$_3$-C$_6$ cycloalkyl, and may be optionally substituted by halogen;

Ⓐ is selected from:

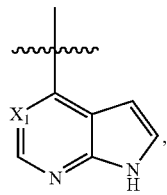

$R^1$ and $R^2$ form a 4-10 membered heterocyclic ring with the carbon atom to which they are attached, wherein one ring carbon atom is replaced by —SO$_2$—, and the ring may be substituted by C$_1$-C$_6$ alkylsulfonyl, C$_1$-C$_6$ alkyl, C$_1$-C$_6$ alkylacyl;

n is selected from 0, 1, 2, 3, 4, 5;

X$_1$ is N, —CR$^5$;

R$^5$ is H, —CN, or halogen;

when X is —CN,

Ⓐ is selected from:

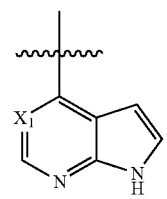

$R^1$ and $R^2$ form a 5-8 membered ring with the carbon atom to which they are attached, wherein one ring carbon atom is replaced by —SO$_2$—, and the ring may be substituted by C$_1$-C$_6$ alkyl, or C$_1$-C$_6$ alkylsulfonyl;

n is selected from 0, 1, 2, 3, 4, 5;

X$_1$ is N, —CR$^5$; and

R$^5$ is H, —CN, or halogen.

2. The compound according to claim 1, wherein said compound has a structure of formula (II):

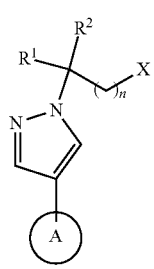

Formula (II)

and an isomer, a solvate, or a pharmaceutically acceptable salt thereof, wherein:

X is —CN,

Ⓐ is selected from:

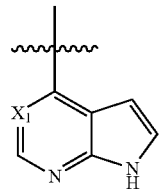

$R^1$ and $R^2$ form a 5-6 membered ring with the carbon atom to which they are attached, wherein one ring carbon atom is replaced by —SO$_2$—, and the ring may further be substituted by C$_1$-C$_6$ alkyl, or C$_1$-C$_6$ alkylsulfonyl;

n is selected from 0, 1, 2, 3, 4, 5;

X$_1$ is N, —CR$^5$; and

R$^5$ is H, —CN, or halogen.

3. The compound according to claim 1, wherein the compound is selected from the following structures:

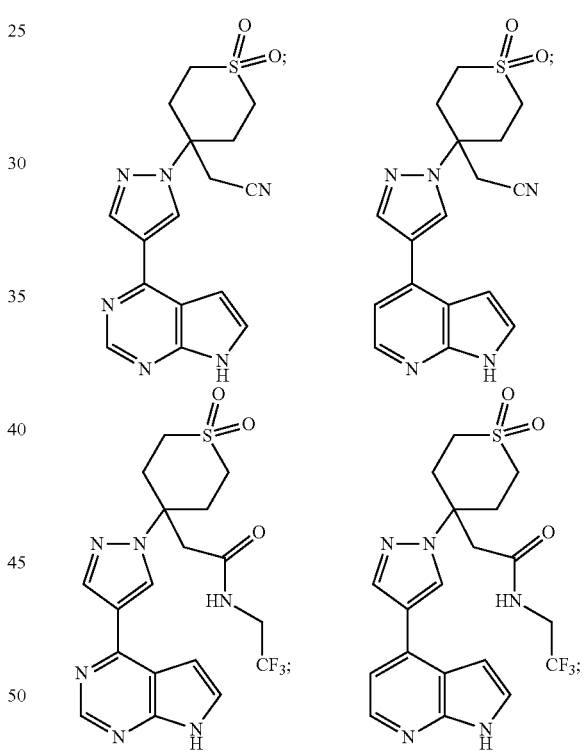

and an isomer, a solvate, or a pharmaceutically acceptable salt thereof.

4. A pharmaceutical composition, comprising a compound, an isomer or a pharmaceutically acceptable salt thereof according to claim 1, and pharmaceutically acceptable carriers.

5. A method of treating a patient suffering with a JAK kinase-associated disease, comprising administering to the patient a compound according to claim 1.

6. The method according to claim 5, wherein the disease is selected from autoimmune diseases, rheumatoid arthritis, multiple sclerosis, psoriatic arthritis, an inflammatory bowel disease, myasthenia gravis, psoriasis.

* * * * *